US008673285B2

(12) United States Patent
Barenholz et al.

(10) Patent No.: US 8,673,285 B2
(45) **Date of Patent: *Mar. 18, 2014**

(54) SPHINGOID POLYALKYLAMINE CONJUGATES FOR VACCINATION

(75) Inventors: Yechezkel Barenholz, Jerusalem (IL); Aviva Joseph, Jerusalem (IL); Eliezer Kedar, Jerusalem (IL)

(73) Assignees: Yissum Research Development Company of the Hebrew University of Jerusalem Ltd., Jerusalem (IL); Biolab Ltd., Jerusalem (IL)

( * ) Notice: Subject to any disclaimer, the term of this patent is extended or adjusted under 35 U.S.C. 154(b) by 976 days.

This patent is subject to a terminal disclaimer.

(21) Appl. No.: 10/560,928

(22) PCT Filed: Jun. 17, 2004

(86) PCT No.: PCT/IL2004/000534

§ 371 (c)(1), (2), (4) Date: May 5, 2006

(87) PCT Pub. No.: WO2004/110496

PCT Pub. Date: Dec. 23, 2004

(65) Prior Publication Data

US 2006/0252717 A1 Nov. 9, 2006

Related U.S. Application Data

(60) Provisional application No. 60/479,185, filed on Jun. 18, 2003, provisional application No. 60/505,638, filed on Sep. 25, 2003, provisional application No. 60/537,553, filed on Jan. 21, 2004, provisional application No. 60/545,505, filed on Feb. 19, 2004.

(51) Int. Cl.
*A61K 31/74* (2006.01)
*A61K 48/00* (2006.01)

(52) U.S. Cl.
USPC ............ 424/78.27; 514/78; 514/44; 525/540; 424/206.1

(58) Field of Classification Search
None
See application file for complete search history.

(56) References Cited

U.S. PATENT DOCUMENTS

| | | | | |
|---|---|---|---|---|
| 4,897,355 | A | 1/1990 | Eppstein et al. | |
| 5,171,678 | A | 12/1992 | Behr et al. | |
| 5,334,761 | A | 8/1994 | Gebeyehu et al. | |
| 5,659,011 | A | 8/1997 | Waldmann | |
| 5,674,908 | A | 10/1997 | Haces et al. | |
| 5,783,565 | A | 7/1998 | Lee et al. | |
| 6,075,012 | A | 6/2000 | Gebeyehu et al. | |
| 6,117,653 | A | 9/2000 | Thoma et al. | |
| 6,281,371 | B1 | 8/2001 | Kloesel et al. | |
| 6,300,321 | B1 | 10/2001 | Scherman et al. | |
| 7,771,711 | B2 * | 8/2010 | Barenholz et al. | 424/78.27 |
| 2001/0048939 | A1 | 12/2001 | Erbacher et al. | |
| 2002/0188023 | A1 * | 12/2002 | Jorgensen et al. | 514/552 |
| 2006/0252718 | A1 | 11/2006 | Barenholz et al. | |
| 2007/0264273 | A1 | 11/2007 | Barenholz et al. | |

FOREIGN PATENT DOCUMENTS

| | | | |
|---|---|---|---|
| EP | 0 394 111 | A1 | 10/1990 |
| JP | 01-213858 | | 8/2001 |
| WO | 95/21175 | A1 | 8/1995 |
| WO | WO 97/45442 | * | 12/1997 |
| WO | WO 98/05678 | A2 | 2/1998 |
| WO | WO 99/02190 | A | 1/1999 |
| WO | 00/37046 | A1 | 6/2000 |
| WO | 01/38295 | A1 | 5/2001 |
| WO | WO 01/38295 | * | 5/2001 |
| WO | 01/48233 | A1 | 7/2001 |
| WO | WO 03/066068 | A1 | 8/2003 |
| WO | 2004/110496 | A1 | 12/2004 |
| WO | 2004/110499 | A1 | 12/2004 |
| WO | 2004/110980 | A1 | 12/2004 |

OTHER PUBLICATIONS

Joseph et al. Vaccine, 2006, vol. 24, p. 3990-4006.*
Jarvis et al., (The Journal of Biological Chemistry 1996, vol. 271, p. 8275-8284.*
International Search Report mailed Oct. 22, 2004 (corresponding PCT Appln. No. PCT/IL2004/000533).
International Search Report mailed Nov. 16, 2004 (corresponding PCT Appln. No. PCT/IL2004/000534).
International Search Report mailed Oct. 22, 2004 (corresponding PCT Appln. No. PCT/IL2004/000536).
Australian Patent Office Examination Report mailed Jun. 30, 2006 (corresponding Singapore Application No. SG200508078-3).
F. Brunel et al., “Cationic lipid DC-Chol induces an improved and balanced immunity able to overcome the unresponsiveness to the hepatitis B vaccine”, *Vaccine* vol. 17, pp. 2192-2203, 1999.
K. Ewert et al., “Efficient Synthesis and Cell-Transfection Properties of a New Multivalent Cationic Lipid for Nonviral Gene Delivery”, *J. Med. Chem.* vol. 45, pp. 5023-5029, 2002.
P. L. Felgner et al., “Lipofection: A highly efficient, lipid-mediated DNA-transfection procedure”, *Proc. Natl. Acad. Sci. USA.*, vol. 84, pp. 7413-7417, Nov. 1987.
X. Gao et al., “A Novel Cationic Liposome Reagent for Efficient Transfection of Mammalian Cells”, *Biochim. Biophys. Acta.* vol. 179, pp. 280-285, 1999.
B. Guy et al., “Design, characterization and preclinical efficacy of a cationic lipid adjuvant for influenza split vaccine”, *Vaccine*, vol. 19, pp. 1794-1805, 2001.

(Continued)

*Primary Examiner* — Agnieszka Boesen
(74) *Attorney, Agent, or Firm* — Browdy and Neimark, PLLC

(57) ABSTRACT

The present invention concerns the use of a sphingoid-poly-alkylamine conjugate as a capturing agent of biologically active molecules, such as antigens. In a particular embodiment, the spinogid-polyalkylamines are used for the preparation of pharmaceutical composition for modulating the immune response of a subject. Other aspects of the invention concern methods for modulating the immune response of a subject by the use of the conjugate, complexes comprising, the sphingoid-polyalkylamine conjugate in combination with a biologically active molecule capable of modulating an immune response of a subject, compositions comprising the conjugate as well as kits making use of said conjugate. A preferred conjugate according to the invention is N palmitoyl D-erythro sphingosyl 1 carbamoyl spermine.

49 Claims, 6 Drawing Sheets

(56) References Cited

OTHER PUBLICATIONS

M. A. Ilies et al., "Recent developments in cationic lipid-mediated gene delivery and gene therapy", *Expert. Opin. Ther. Patents.*, vol. 11, No. 11, pp. 1729-1752, 2001.
K. M. Lima et al., "Comparison of different delivery systems of vaccination for the induction of protection against tuberculosis in mice", *Vaccine*, vol. 19, pp. 3518-3525, 2001.
A. D. Miller, "Cationic Liposomes for Gene Therapy", *Chem. Int.* Ed. Eng., vol. 37, pp. 1768-1785, 1987.
T. Nakanishi et al., "Positively charged liposome functions as an efficient immunoadjuvant in inducing cell-mediated immune response to soluble proteins", *J. Controlled Release*, vol. 61, pp. 233-240, 1999.
M. Saminathan et al., "Ionic and Structural Specificity Effects of Natural and Synthetic Polyamines on the Aggregation and Resolubilization of Single-, Double-, and Triple-stranded DNA", *Biochemistry*, vol. 38, pp. 3821-3830, 1999.
Diminsky et al., "Comparison between hepatitis B surface antigen (HBsAg) particles derived from mammalian cells (CHO) and yeast cells (Hansenula polymorpha): composition, structure and immuDogenicity" Vaccine, vol. 15, 6/7:637-647 (1997).
Valenzuela et al., "Synthesis and assembly of hepatitis B virus surface antigen particles in yeast" Nature, 298:22 (1982).
U.S. Appl. No. 10/560,932, filed May 5, 2006.
Official Action dated Aug. 24, 2010, in U.S. Appl. No. 10/560,932.
U.S. Appl. No. 11/345,624, filed Feb. 2, 2006.
Alving CR. Liposomes as adjuvants for vaccines. Immunol Rev 1995;145:5-31.
Alving CR. Liposomal vaccines: clinical status and immunological presentation for humoral and cellular immunity. Ann NY Acad Sci 1995;754:143-52.
Babai et al. "A novel influenza subunit vaccine composed of liposome-encapsulated haemagglutinin/neuraminidase and IL-2 or GM-CSF. I. Vaccine characterization and efficacy studies in mice" Vaccine 1999;17:1223-38.
Babai et al. "A novel influenza subunit vaccine composed of liposome-encapsulated haemagglutinin/neuraminidase and IL-2 or GM-CSF. II. Induction of TH1 and TH2 responses in mice" Vaccine 1999;17:1239-50.
Cox et al. "Adjuvants—a classification and review of their modes of action" Vaccine 1997;15:248-56.
Foged et al. "Interaction of dendritic cells with antigen-containing liposomes: effect of bilayer composition" Vaccine 2004;22:1903-13.
Garbuzenko et al. "Effect of grafted PEG on liposome size and on compressibility and packing of lipid bilayer" Chem Phys Lipids 2005;135:117-29.
Gregoriadis G. "The immunological adjuvant and vaccine carrier properties of liposomes" J Drug Target 1994;2:351-6.
Israelachvili et al. "Physical principles of membrane organization" Q Rev Biophys 1980;13:121-200.
Itskovitz-Cooper et al. "A new intranasal influenza vaccine based on a novel polycationic lipid—ceramide carbamoylspermine (CCS) I. Immunogenicity and efficacy studies in mice"Vaccine 2006;24:3990-4006.
Laing et al. "The 'co-delivery' approach to liposomal vaccines: application to the develop ment of influenza-A and hepatitis-B vaccine candidates" J Liposome Res 2006;16:229-35.
Lonez et al. "Cationic liposomal lipids: from gene carriers to cell signaling" Prog Lipid Res 2008;47:340-7.
Miller et al. "Liposome-cell interactions in vitro: effect of liposome surface charge on the binding and endocytosis of conventional and sterically stabilized liposomes" Biochemistry 1998;37:12875-83.
Nakanishi et al."Positively charged liposome functions as an efficient immunoadjuvant in inducingimmuneresponses to soluble proteins" Biochem Biophys ResCommun 1997;240:793-7.
Perrie et al. "Liposome-mediated DNA vaccination: the effect of vesicle composition" Vaccine 2001;19:3301-10.
Schwendener et al. "The effects of charge and size on the interaction of unilamellar liposomes with macrophages" Biochim Biophys Acta 1984;772:93-101.
Simberg et al. "DOTAP (and other cationic lipids): chemistry, biophysics, and transfection" Crit Rev Ther Drug Carrier Syst 2004;21(4):257-317.
Storm et al. "Liposomes: quo vadis?" Pharm Sci Technol Today 1998;1:19-31.
Yan et al. "Mechanism of adjuvant activity of cationic liposome: phosphorylation of a MAP kinase, ERK and induction of chemokines"Mol Immunol 2007;44:3672-81.
Zhou et al. "Liposome-mediated cytoplasmic delivery of proteins: an effective means of accessing the MHC class I-restricted antigen presentation pathway" Immunomethods 1994;4:229-35. (Abstract Only).
Bangham, "Liposomes: realizing their promise." Hosp Pract (Off Ed). 15;27(12):51-6, 61-2 (1992) (Abstract).
Cabral et al., "Cellular and Humoral Immunity in Guinea Pigs to Two Major Polypeptides Derived from Hepatitis B Surface Antigen" J. gen. Virol. 38, 339-350 (1978).
Diminsky et al., "Structural and Functional Characterization of Liposomal Recombinant Hepatitis B Vaccine" Journal of Liposome Research 6(2), 289-304 (1996).
Fellowes et al. "Amelioration of established collagen induced arthritis by systemic IL-10 gene delivery" Gene Therapy 7, 967-977 (2000).
Fletcher et al. "A dialkynoyl analogue of DOPE improves gene transfer of lowercharged, cationic lipoplexes", Org Biomol Chem. 21; 4(2):196-9 (2006) (Abstract).
Gavilanes et al., "Hepatitis B surface antigen—Role of lipids in maintaining the structural and antigenic properties of protein components" Biochem. J. 265, 857-864 (1990).
Gomez-Gutierrez et al., "Reconstitution of hepatitis B surface antigen proteins into phospholipid vesicles" Biochimica et Biophysica Acta 1192: 45-52 (1994).
Hermanson., "Bioconjugate Techniques" Academic Press, San Diego, CA, pp. 154-155 (1996).
Keller et al. "Thermodynamic aspects and biological profile of CDAN/DOPE and DC-Chol/DOPE lipoplexes" Biochemistry 27; 42(20):6067-77 (2003) (Abstract).
Even-Or et al. "Immunogenicity, protective efficacy and mechanism of novel CCS adjuvanted influenza vaccine" Vaccine 28:6527-6541 (2010).
Even-Or et al. "A new intranasal influenza vaccine based on a novel polycationic lipid-ceramide carbamoyl-spermine (CCS). II. Studies in mice and ferrets and mechanism of adjuvanticity" Vaccine 29:2474-2486 (2011).

* cited by examiner

SPHINGOID POLYALKYLAMINE CONJUGATES FOR VACCINATION

FIELD OF THE INVENTION

The present invention concerns vaccination making use of sphingolipids' polyalkylamine conjugates for effective delivery of biologically active materials, in particular, antigenic molecules.

LIST OF PRIOR ART

The following is a list of prior art which is considered to be pertinent for describing the state of the art in the field of the invention.

U.S. Pat. No. 5,334,761: "Cationic lipids";
US 2001/048939: "Cationic reagents of transfection";
U.S. Pat. No. 5,659,011: "Agents having high nitrogen content and high cationic charge based on dicyanimide dicyandiamide or guanidine and inorganic ammonium salts";
U.S. Pat. No. 5,674,908: "Highly packed polycationic ammonium, sulfonium and phosphonium lipids";
U.S. Pat. No. 6,281,371: "Lipopolyamines, and the preparation and use thereof";
U.S. Pat. No. 6,075,012: "Reagents for intracellular delivery of macromolecules";
U.S. Pat. No. 5,783,565: "Cationic amphiphiles containing spermine or spermidine cationic group for intracellular delivery of therapeutic molecules";
Marc Antoniu Ilies & Alexandru T. Balaban, Expert Opin. Ther. Patents. 11(11):1729-1752 (2001);
Miller A D. Chem. Int. Ed. Eng. 37:1768-1785 (1998);
Nakanichi T. et al. J. Control Release 61:233-240 (1999);
Brunel F. et al. Vaccine 17:2192-2193 (1999);
Guy B. et al. Vaccine 19:1794-1805 (2001);
Lima K M et al. Vaccine 19:3518-3525 (2001).

BACKGROUND OF THE INVENTION

Many natural biological molecules and their analogues, including proteins and polynucleotides, foreign substances and drugs, which are capable of influencing cell function at the sub-cellular or molecular level are preferably incorporated within the cell in order to produce their effect. For these agents the cell membrane presents a selective barrier which is impermeable to them. The complex composition of the cell membrane comprises phospholipids, glycolipids, and cholesterol, as well as intrinsic and exrinsic proteins, and its functions are influenced by cytoplasmic components which include $Ca^{++}$ and other metal ions, anions, ATP, microfilaments, microtubules, enzymes, and $Ca^{++}$-binding proteins, also by the extracellular glycocalyx (proteoglycans, glycose aminoglycans and glycoproteins). Interactions among structural and cytoplasmic cell components and their response to external signals make up transport processes responsible for the membrane selectivity exhibited within and among cell types.

Successful delivery of agents not naturally taken up by cells into cells has also been investigated. The membrane barrier can be overcome by associating agents in complexes with lipid formulations closely resembling the lipid composition of natural cell membranes. These formulations may fuse with the cell membranes on contact, or what is more common, taken up by pynocytosis, endocytosis and/or phagocytosis. In all these processes, the associated substances are delivered in to the cells.

Lipid complexes can facilitate intracellular transfers also by overcoming charge repulsions between the cell surface, which in most cases is negatively charged. The lipids of the formulations comprise an amphipathic lipid, such as the phospholipids of cell membranes, and form various layers or aggregates such as micelles or hollow lipid vesicles (liposomes), in aqueous systems. The liposomes can be used to entrap the substance to be delivered within the liposomes; in other applications, the drug molecule of interest can be incorporated into the lipid vesicle as an intrinsic membrane component, rather than entrapped into the hollow aqueous interior, or electrostatically attached to aggregate surface. However, most phospholipids used are either zwiterionic (neutral) or negatively charged.

An advance in the area of intracellular delivery was the discovery that a positively charged synthetic cationic lipid, N-[1-(2,3-dioleyloxy)propyl]-N,N,N-trimethylammonium chloride (DOTMA), in the form of liposomes, or small vesicles, could interact spontaneously with DNA to form lipid-DNA complexes which are capable of adsorbing to cell membranes and being taken up by the cells either by fusion or more probably by adsorptive endocytosis, resulting in expression of the transgene [Felgner, P. L. et al. Proc. Natl. Acad. Sci., USA 84:7413-7417 (1987) and U.S. Pat. No. 4,897,355 to Eppstein, D. et al.]. Others have successfully used a DOTMA analogue, 1,2-bis(oleoyloxy)-3-(trimethylammonio)propane (DOTAP) in combination with a phospholipid to form DNA-complexing vesicles. The Lipofectin™ reagent (Bethesda Research Laboratories, Gaithersburg, Md.), an effective agent for the delivery of highly anionic polynucleotides into living tissue culture cells, comprises positively charged liposomes composed of positively charged lipid DOTMA and a neutral lipid dioleyl phosphatidyl ethanol amine (DOPE) referred to as helper lipids. These liposomes interact spontaneously with negatively charged nucleic acids to form complexes, referred to as lipoplexes. When excess of positively charged liposomes over DNA negative charges are used, the net charge on the resulting complexes is also positive. Positively charged complexes prepared in this way spontaneously attach to negatively charged cell surfaces or introduced into the cells either by adsorptive endocytosis or fuse with the plasma membrane, both processes deliver functional polynucleotide into, for example, tissue culture cells. DOTMA and DOTAP are good examples for monocationic lipids. [Illis et al. 2001, ibid.]

Multivalent cations by themselves (including polyamines, inorganic salts and complexes and dehydrating solvents) have also been shown to facilitate delivery of macromolecules into cells. In particular, multivalent cations provoke the collapse of oligo and polyanions (nucleic acids molecules, amino acid molecules and the like) to compact structural forms, and facilitate the packaging of these polyanions into viruses, their incorporation into liposomes, transfer into cells etc. [Thomas T. J. et al. Biochemistry 38:3821-3830 (1999)]. The smallest natural polycations able to compact DNA are the polyamines spermidine and spermine. By attaching a hydrophobic anchor to these molecules via a linker, a new class of transfection vectors, the polycationic lipopolymers, has been developed.

Cationic lipids and cationic polymers interact electrostatically with the anionic groups of DNA (or of any other polyanionic macromolecule) forming DNA-lipid complexes (lipoplexes) or DNA-polycation complexes (polyplexes). The formation of the complex is associated with the release of counterions of the lipids or polymer, which is the thermodynamic driving force for lipoplex and polyplex spontaneous formation. The cationic lipids can be divided into four classes: (i) quaternary ammonium salt lipids (e.g. DOTMA (Lipofectin™) and DOTAP) and phosphonium/arsonium congeners; (ii) lipopolyamines; (iii) cationic lipids bearing both quaternary ammonium and polyamine moieties and (iv) amidinium, guanidinium and heterocyclic salt lipids.

SUMMARY OF THE INVENTION

According to one of its aspects, the present invention concerns the use of a sphingoid-polyalkylamine conjugate for the preparation of a pharmaceutical composition for modulating the immune response of a subject.

According to a preferred embodiment, the sphingoid-polyalkylamine conjugate comprises a sphingoid backbone carrying, via a carbamoyl bond at least one polyalkylamine chain polyalkylamine chain.

The term sphingoid-polyalkylamine conjugate as used herein denotes chemical conjugation (linkage) between a sphingoid base (herein also referred to by the term "sphingoid backbone") and at least one polyalkylamine chain. The conjugation between the sphingoid base and the at least one polyalkylamine chain is via a carbamoyl bond, as further detailed hereinafter.

The sphingoid base/backbone, as used herein, includes, long chain aliphatic amines, containing two or three hydroxyl groups, the aliphatic chain may be saturated or unsaturated. One example of an unsaturated sphingoid base is that containing a distinctive trans-double bond in position 4.

The term modulating as used herein denotes any measurable regulatory or biochemical effect exhibited by the biologically active material delivered by the conjugate, on a subject's immune response, including cellular response and/or humoral response. Modulation includes inhibition or, on the other hand, stimulation or enhancement of either or both types of responses when the sphingoid-polyalkylamine conjugate is administered to said subject in combination with a biologically active substance. The modulation preferably refers to stimulation or enhancement by a factor of two or more, relative to that elicited by the biological active molecule administered without the conjugate. The invention also concerns the modulation of an immune response in cases when the biologically active material administered without the conjugate is substantially ineffective in producing such a response.

Yet further, modulation concerns inhibition or suppression of the immune response of a subject, e.g. for the treatment of auto-immune diseases as well as for the treatment of allergy.

Thus, the term biologically active molecule as used herein denotes any substance which, when administered in combination with the sphingoid-polyalkylamine conjugate has an effect on the immune system of a subject. The biologically active material is preferably an antigenic protein, antigenic peptide, antigenic polypeptide or antigenic carbohydrate.

According to another aspect, the present invention concerns a method for modulating the immune response of a subject, the method comprises providing said subject with a sphingoid-polyalkylamine conjugate together with a biologically active molecule, said sphingoid-polyalkylamine conjugate comprises a sphingoid backbone carrying, via a carbamoyl bond at least one polyalkylamine chain.

According to yet another aspect, the present invention concerns a pharmaceutical composition for modulating the immune response of a subject, the composition comprises: (i) at least one sphingoid-polyalkylamine conjugate; and (ii) at least one biologically active molecule associated with said conjugate.

According to yet another embodiment, the invention provides a complex comprising: (i) a sphingoid-polyalkylamine conjugate and (ii) a biologically active material capable of modulating an immune response of a subject.

Finally, the invention concerns the use of

Finally, the invention concerns the use of a sphingoid-polyalkylamine conjugate as defined, as a capturing agent of biologically-active molecules (e.g. antigenic molecules). In this context, the sphingoid-polyalkylamine conjugate may form part of a kit for capturing biologically active molecules, preferably antigenic molecules and/or immunostimulants, and/or immunosuppressants, the kit comprising, in addition to said conjugate, instructions for use of same for capturing the biologically active molecules. The conjugate in the kit may be in a dry form, in which case, the kit may also include a suitable fluid with which the conjugate is mixed prior to use to form a suspension or emulsion or solution, or it may already be in a fluid (suspension, emulsion, solution, etc.) form. The kit may have numerous applications. For example, the kit may be used for investigating the function of different immunomodulating molecules in modulation of immune responses, for isolation of active biological molecules, and identification thereof. Those versed in the art will know how to make use of such a capturing agent also for research purposes.

The term capturing agent as used herein refers to the conjugate being capable of associating with biologically active molecules, the latter having a negative charge, a negative dipole or a local negative charge (an area within the molecule carrying a net negative charge), by virtue of the conjugate's polycationic structure. The capturing per se involves electrostatic interaction between the molecule to be captured, carrying said negative charge, negative dipole or local negative charge and the positively charged conjugate of the invention.

The conjugate of the invention may also be used as a delivery vehicle, carrying, by capturing thereto, biologically active molecules to a target site and into a target cell.

BRIEF DESCRIPTION OF THE FIGURES

In order to understand the invention and to see how it may be carried out in practice, some embodiments will now be described, by way of non-limiting examples only, with reference to the accompanying figures, in which:

FIGS. 1A-1D show several possible chemical structures, "linear", branched" or "cyclic" lipid like cationic (LLC) compounds which are encompass under the general definition of sphingoid-polyalkylamine conjugate of formula (I), wherein FIG. 1A shows a sphingoid backbone (ceramide) linked to a single polyalkylamine chain, FIG. 1B and FIG. 1C show the same sphingoid backbone linked to two polyalkylamine chains, FIG. 1D shows again the same backbone, however, in which a single polyalkylamine chain is linked via the two hydroxyl moieties to form a cyclic polyalkylamine conjugate.

FIG. 2A shows distribution of empty DMPC:DMPG (mole ratio 9:1); FIG. 2B shows distribution of DMPC:DMNG:HN; FIG. 2C shows distribution of empty DOTAP:cholesterol; FIG. 2D shows distribution of DOTAP:cholesterol:HN; FIG. 2E shows distribution of empty CCS:cholesterol; and finally, FIG. 2F shows distribution of CCS-cholesterol:HN.

FIG. 3A shows bio-distribution of free $^{125}$I-HN; FIG. 3B shows $^{125}$I-HN loaded lipid assembly composed of DOTAP:Cholesterol; FIG. 3C shows $^{125}$I-HN loaded lipid assembly composed of DMPC:DMPG and FIG. 3D shows $^{125}$I-HN loaded lipid assembly composed of CCS:Cholesterol.

DETAILED DESCRIPTION OF THE INVENTION

Figure 1A:
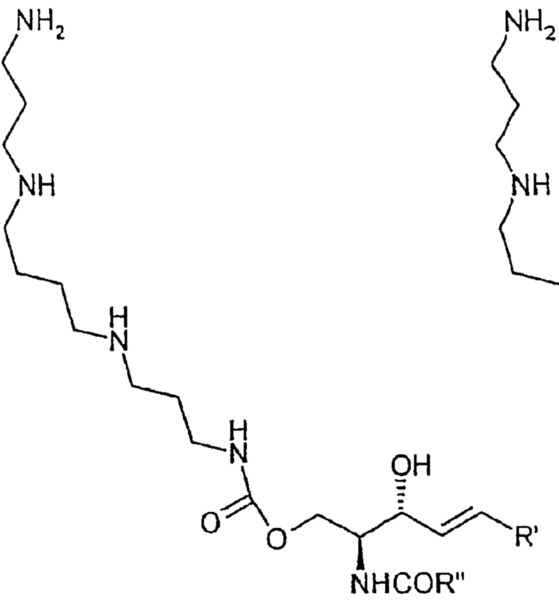

The present invention concerns the use of sphingoid-polyalkylamine conjugates as capturing agents for carrying biologically active molecules which are effective in modulating the immune response of a subject.

The sphingoid-polyalkylamine conjugates are lipid-like cationic (LLC) compounds, which may be synthesized in the following manner. N-substituted long-chain bases in particular, N-substituted sphingoids or sphingoid bases are coupled together with different polyalkylamines or their derivatives, to form a polyalkylamine-sphingoid entity, which is used as is, or further alkylated.

Protonation at a suitable pH or alkylation of the formed polyalkylamine-sphingoid entity attributes to the lipid-like compounds a desired positive charge for interaction with biologically active biological molecules to be delivered into target cells and with the targeted cells. The sphingoid-polyalkylamine conjugates may be efficiently associated with the biologically active molecules by virtue of electrostatic interactions between the anionic character of the biologically active molecules and the polyalkylamine moieties of the conjugate to form complexes (lipoplexes).

Alternatively, the sphingoid-polyalkylamine conjugates may form assemblies loaded with the biologically active molecules.

The sphingoid-polyalkylamine conjugate may be in the form individual lipid like molecules or in the form of an assembly. One example of a suitable assembly includes the formation of micelles or vesicles, and in particular, liposomes. Other examples of assemblies include the formation of micelles, inverted phases, cubic phases and the like. Evidently, the sphingoid polyalkylamine conjugate may be in combined vesicle/micelle form or any other combination of assemblies.

Lipid assembly as used herein denotes an organized collection of lipid molecules forming inter alia, micelles and liposomes. The lipid assemblies are preferably stable lipid assemblies. Stable lipid assembly as used herein denotes an assembly being chemically and physically stable under storage conditions (4° C., in physiological medium) for at least one month.

When the assemblies are in the form of vesicles (e.g. liposomes) the biologically active molecule may be encapsulated within the vesicle, part of its lipid bilayer, or adsorbed to the surface of the vesicle (or any combination of these three options). When the assemblies are micelles, the biologically active molecules may be inserted into the amphiphiles forming the micelles and/or associated with it electrostatically, in a stable way.

Thus, as used herein, the terms "encapsulated in", "contained in", "loaded onto" or "associated with" indicate a physical attachment between the conjugate and the biologically active molecule. The physical attachment may be either containment or entrapment of the molecule within assemblies (e.g. (vesicles, micelles or other assemblies) formed from the conjugate; non-covalent linkage of the biological molecule to the surface of such assemblies, or embedment of the biological molecule in between the sphingoid-polyalkylamine conjugates forming such assemblies. It should be noted that due to the positive charge or positive dipole of the sphingoid-polyalkylamine conjugate under physiological conditions, the preferred association between the conjugate and the biologically active material is by electrostatic, dipole or acid-base interactions.

Notwithstanding the above, the invention should not be limited by the particular type of association formed between the sphingoid-polyalkylamine conjugate and the biologically active molecule. Thus, association means any interaction between the conjugate or the assembly formed therefrom and the biologically active material which is capable of achieving a desired therapeutic effect.

The biologically active molecule and the conjugate may be associated by any method known in the art. This includes, without being limited thereto, post- or co-lyophilzation of the conjugate with the biologically active molecule, or by mere mixing of preformed sphingoid-polyalkylamine conjugate with the biological molecule. Method for co-lyophilization are described, inter alia, in U.S. Pat. Nos. 6,156,337 and 6,066,331, while methods for post-encapsulation are described, inter alia, in WO03/000227, all incorporated herein by reference.

Thus, according to a first of its aspects, the present invention concerns the use of a sphingoid-polyalkylamine conjugate for the preparation of a pharmaceutical composition for modulating the immune response of a subject, wherein said sphingoid-polyalkylamine conjugate comprises a sphingoid backbone carrying, via a carbamoyl bond, at least one, and preferably one or two, polyalkylamine chains.

As indicated above, the sphingoid-polyalkylamine conjugate includes a linkage between a sphingoid backbone and at least one polyalkylamine chain, the linkage is via corresponding carbamoyl bonds. More preferably, the sphingoid-polyalkylamine conjugate has the general formula (I):

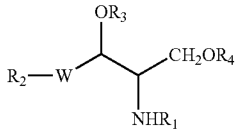

wherein $R_1$ represents a hydrogen, a branched or linear alkyl, aryl, alkylamine, or a group —C(O)$R_5$;

$R_2$ and $R_5$ represent, independently, a branched or linear $C_{10}$-$C_{24}$ alkyl, alkenyl or polyenyl groups;

$R_3$ and $R_4$ are independently a group —C(O)—$NR_6R_7$, $R_6$ and $R_7$ being the same or different for $R_3$ and $R_4$ and represent, independently, a hydrogen, or a saturated or unsaturated branched or linear polyalkylamine, wherein one or more amine units in said polyalkylamine may be a quaternary ammonium; or $R_3$ is a hydrogen; or $R_3$ and $R_4$ form together with the oxygen atoms to which they are bound a heterocyclic ring comprising —C(O)—$NR_9$—[$R_8$—$NR_9$]$_m$—C(O)—, $R_8$ represents a saturated or unsaturated $C_1$-$C_4$ alkyl and $R_9$ represents a hydrogen or a polyalkylamine of the formula —[$R_8$—$NR_9$]$_n$—, wherein said $R_9$ or each alkylamine unit $R_8NR_9$ may be the same or different in said polyalkylamine; and n and m are independently an integer from 1 to 10, preferably 3 to 6;

W represents a group selected from —CH═CH—, —$CH_2$—CH(OH)— or —$CH_2$—$CH_2$—.

Non-limiting examples of the sphingoids or sphingoid bases which may be used according to a more specific embodiment of the invention, include, sphingosines, dihydrosphingosines, phytosphingosines, dehydrophytosphinosine and derivatives thereof. Non-limiting examples of such derivatives are acyl derivatives, such as ceramide (N-acylsphingosine), dihydroceramides, phytoceramides and dihydrophytoceramides, respectively, as well as ceramines (N-alkylsphinogsine) and the corresponding derivatives (e.g. dihydroceramine, phytoceramine etc.). The suitably N-substituted sphingoids or sphingoid bases posses free hydroxyl groups which are activated and subsequently reacted with the polyalkylamines to form the polyalkylamine-sphingoid entity. Non-limiting examples of activation agents are N,N'-disuccinimidylcarbonate, di- or tri-phosgene or imidazole derivatives. The reaction of these activation agents with the sphingoids or the sphingoid bases yields a succinimidyloxycarbonyl, chloroformate or imidazole carbamate, respectively, at one or both hydroxyls. The reaction of the activated sphingoids with polyalkylamines may yield branched, straight (unbranched) or cyclic conjugates as shown in FIG. 1.

Figure 1B:
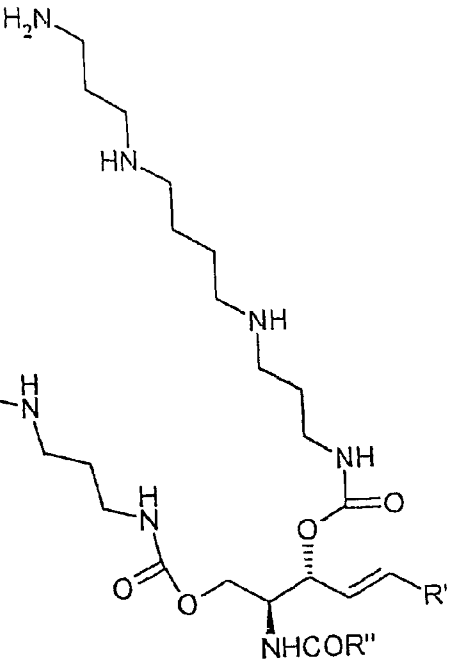
Figure 1C:
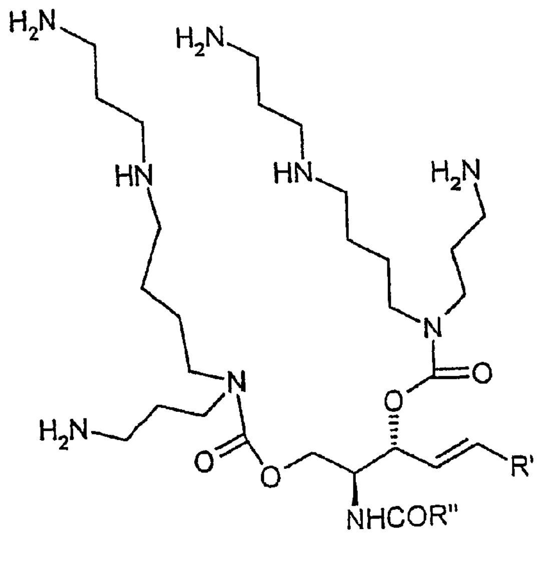
Figure 1D:
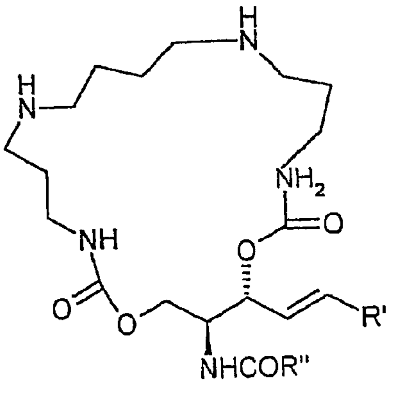
Figure 2A:
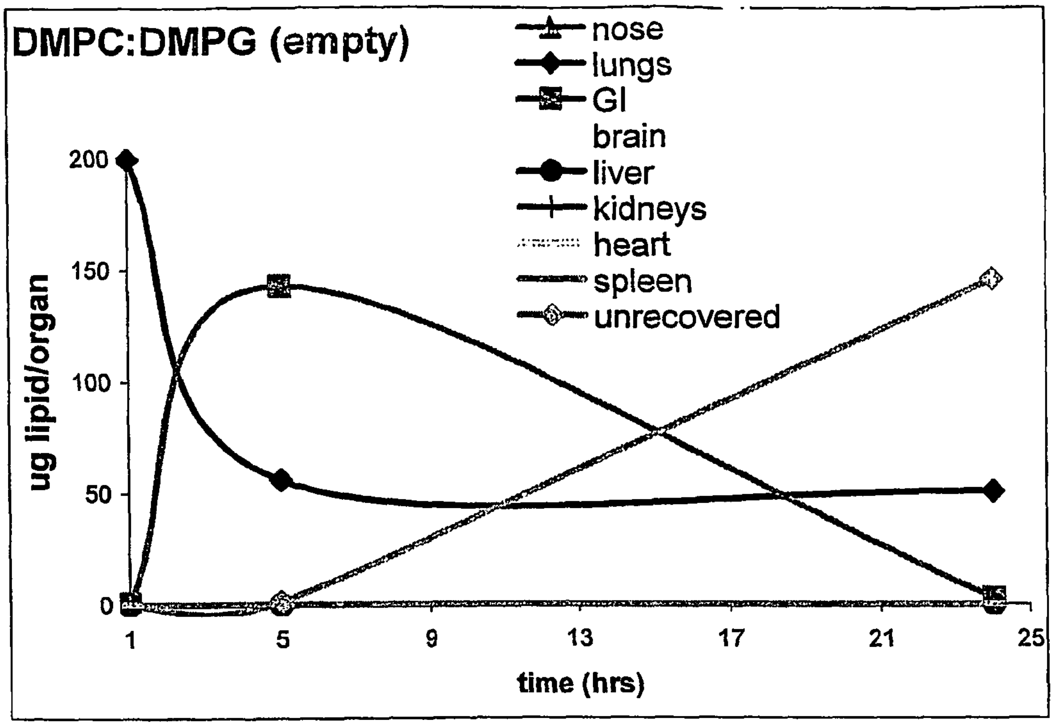
FIGS. 2A-2F show the bio-distribution and pharmacokinetics of various fluorescently-labeled lipid formulations in the GI-■-, lungs -♦- or spleen --- with unrecovered -♦-.
Figure 2B:
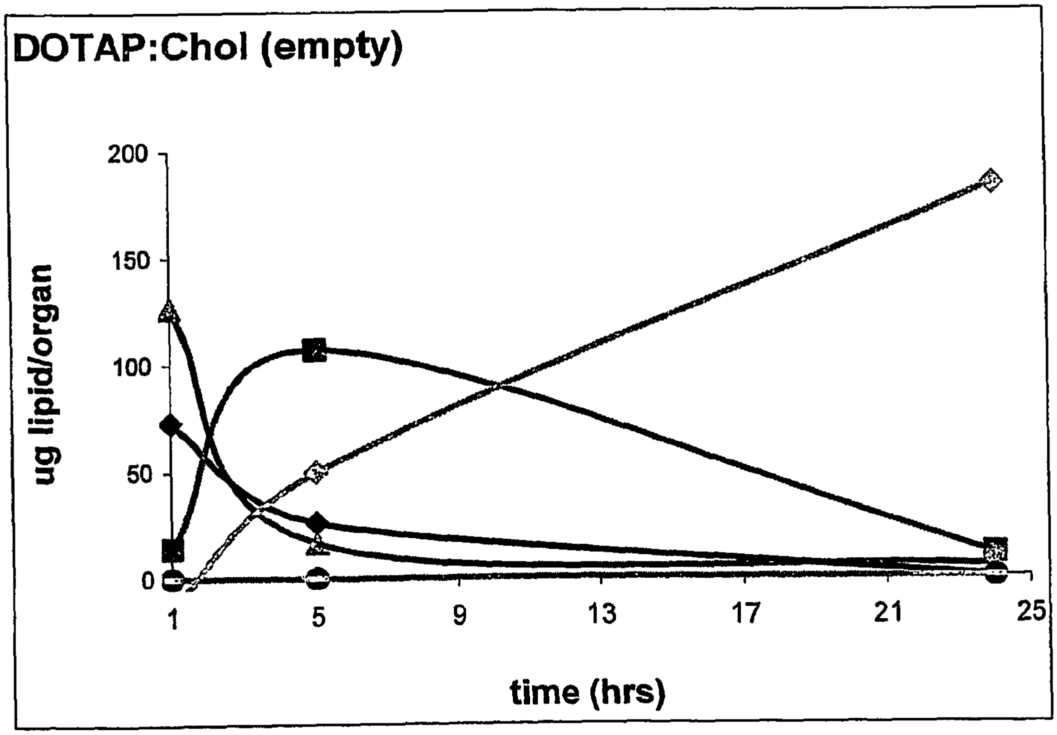
Figure 2C:
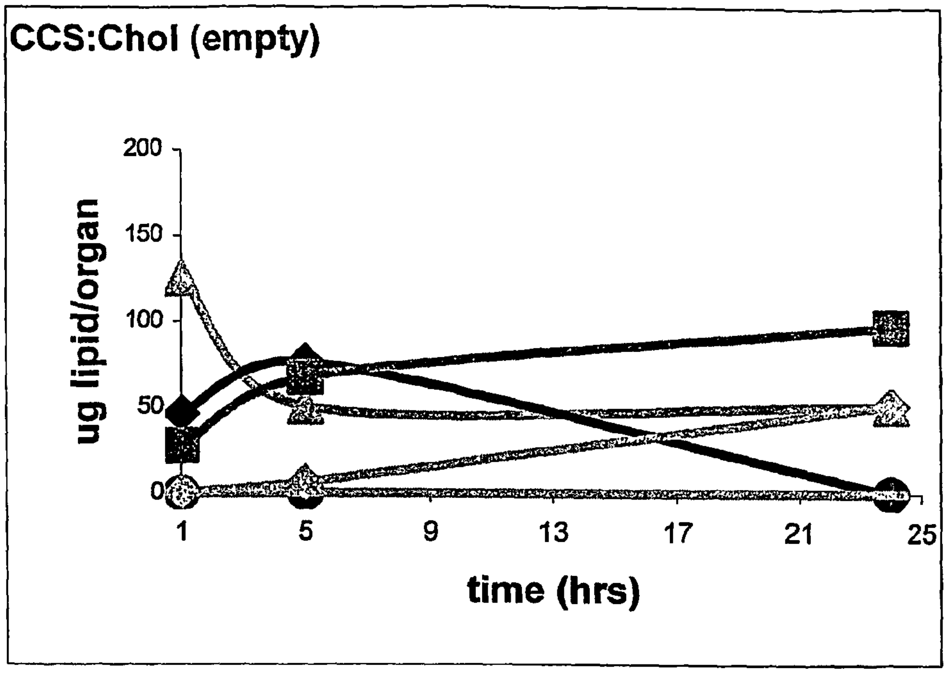
Figure 2D:
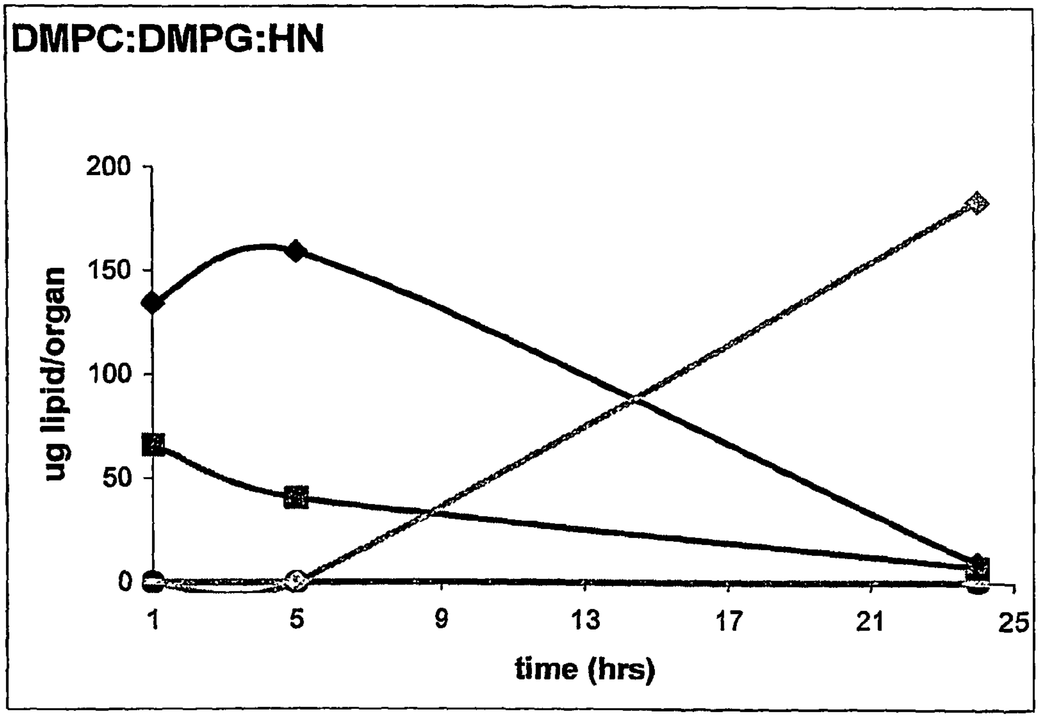
Figure 2E:
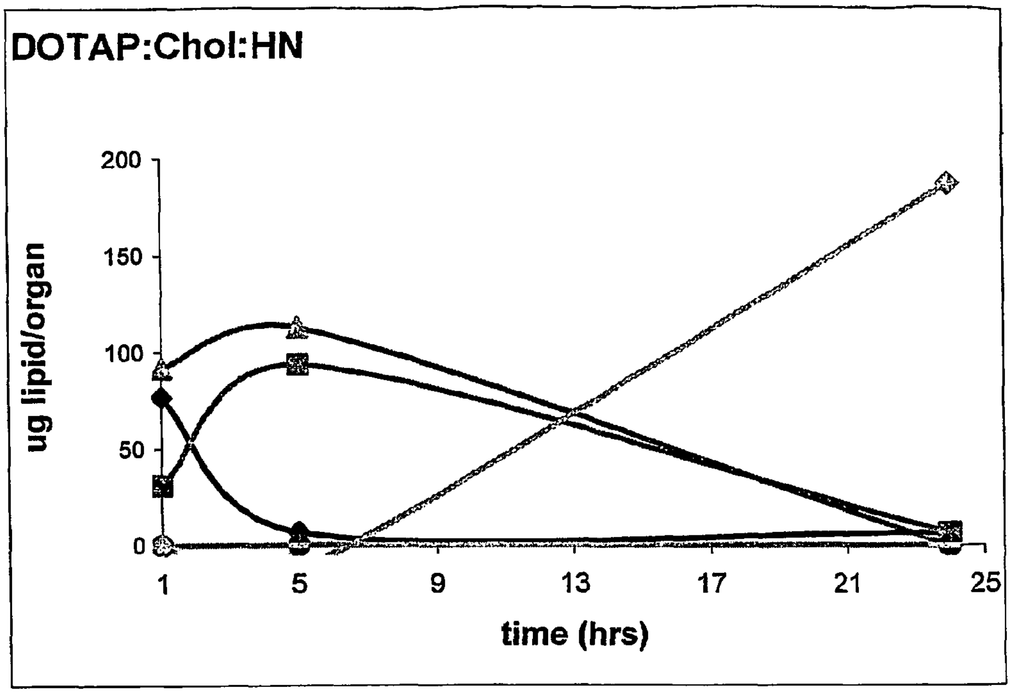
Figure 2F:
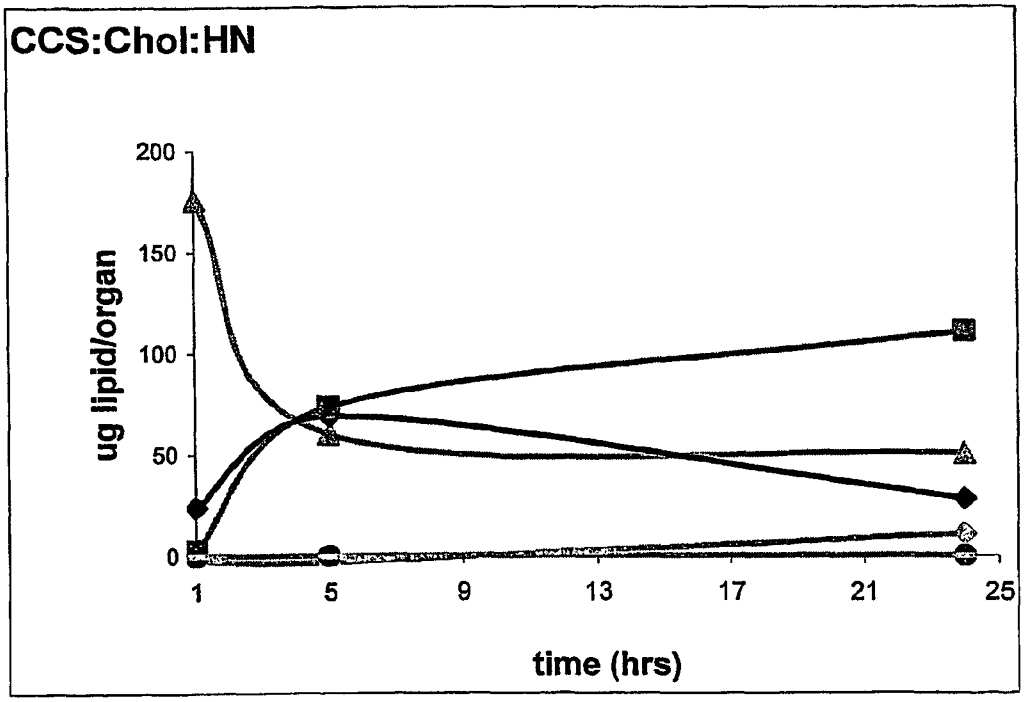
Figure 3A:
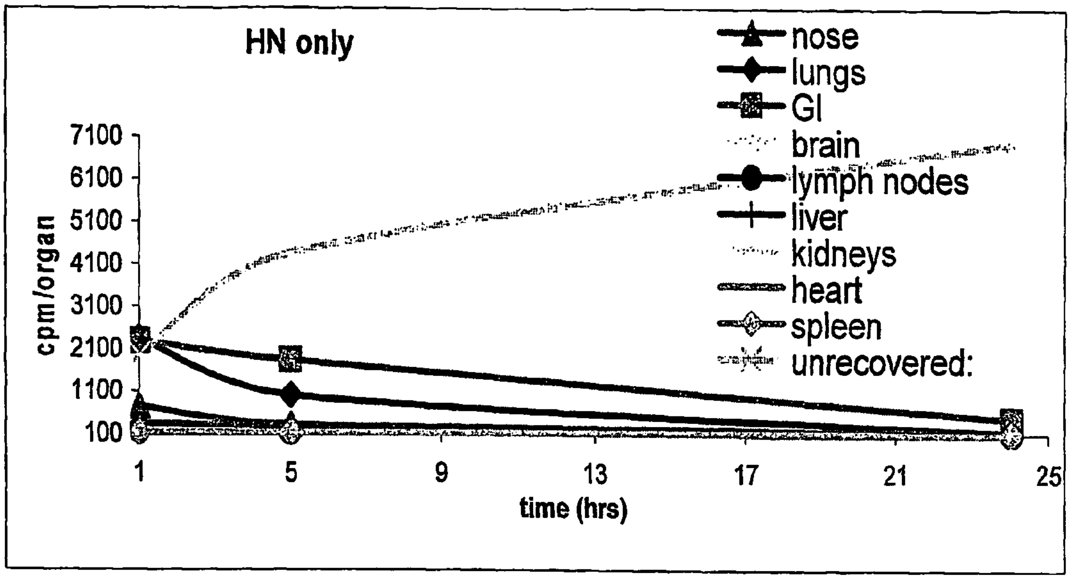
FIGS. 3A-3D show bio-distribution of various $^{125}$I-HN loaded lipid assembly formulations in the GI-■-, lungs -♦- or spleen - ◇ - with unrecovered -x-, and in particular.
Figure 3B:
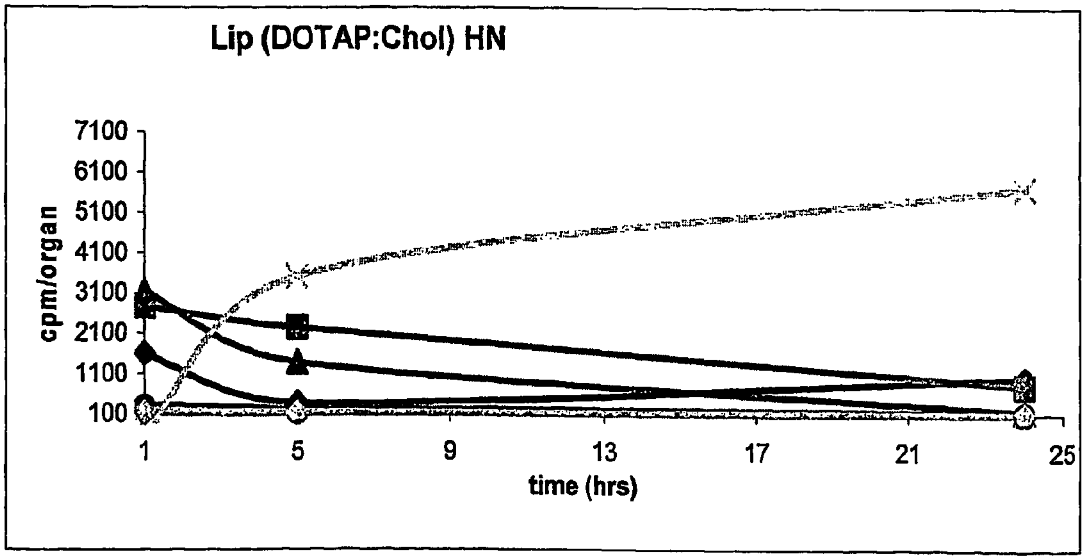
Figure 3C:
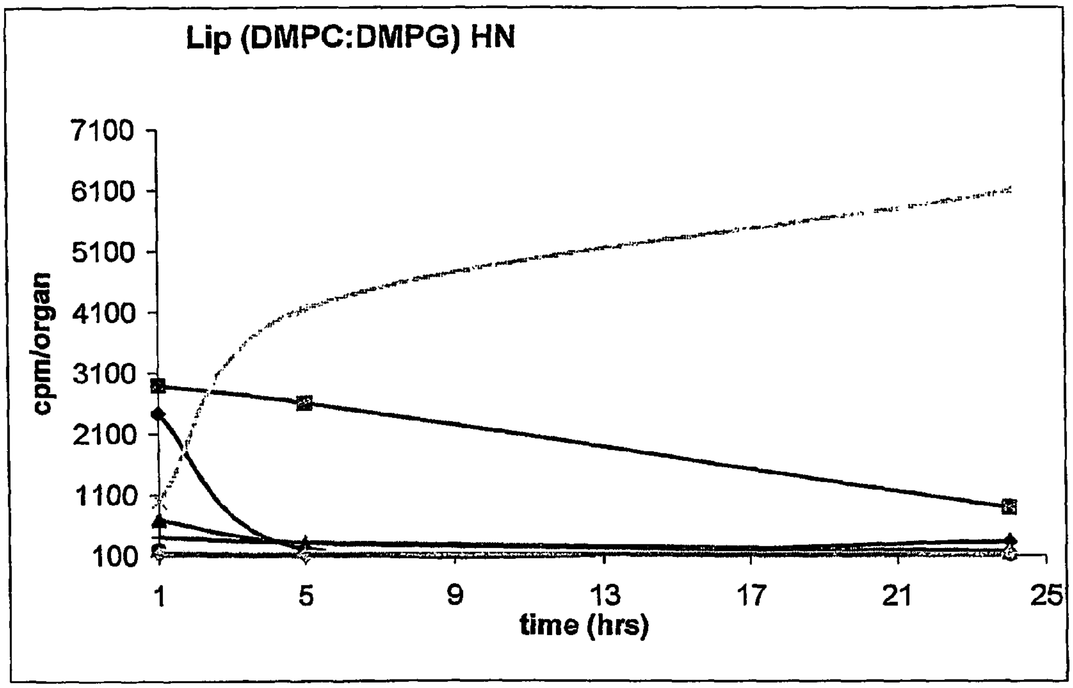
Figure 3D:
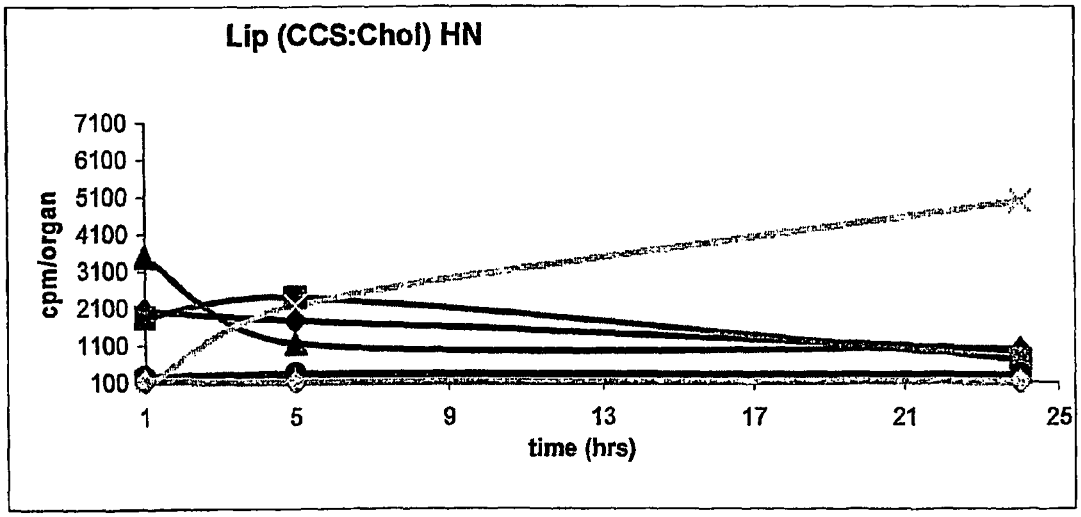

According to one preferred embodiment the sphingoid backbone is a ceramide linked to one (FIG. 1A) or two (FIG. 1B or 1C) polyalkylamine chains, or linked via the two hydroxyl moieties to form a cyclic polyalkylamine moiety (FIG. 1D).

The formed sphingoid-polyalkylamine conjugates may be further reacted with methylation agents in order to form quaternary amines. The resulting compounds are positively charged to a different degree depending on the ratio between the quaternary, primary and/or secondary amines within the formed conjugates. As such, the sphingoid-polyalkylamine conjugate exists as quaternized nitrogen salt including, but not limited to, quaternary ammonium chloride, a quaternary ammonium iodide, a quaternary ammonium fluoride, a quaternary ammonium bromide, a quaternary ammonium oxyanion and a combination thereof.

The sphingoid-polyalkylamine conjugate is preferably used in combination with a biologically active molecule. The biologically active material is any molecule which when administered with the sphingoid-polyalkylamine conjugate has an effect on the immune system of a subject, according to one embodiment, a stimulating or enhancing effect. The effect is preferably by a factor of two or more relative to the effect, if any, of the biologically active molecule, when provided to a subject without said conjugate.

According to one embodiment, the biologically active material is a protein, polypeptide, peptide, or carbohydrate. Specifically, the biologically active molecule may be an immunomodulator, including antigenic protein or antigenic peptide, immunostimulants and/or immunosuppressants. Antigenic proteins and peptides, immunostimulants and immunosuppressants are all well known in the art. Preferably, the biologically active protein or peptide or carbohydrate has at a physiological pH either a net negative dipole moment, a net negative charge or contains at least one region having a net negative charge negatively charged.

According to yet another embodiment, the biologically active material is a nucleic acid molecule, such as oligodeoxynucleotides (ODN).

A preferred weight ratio between the sphingoid-polyalkylamine conjugate and biologically active material is 1000:1 to 1:1 weight ratio.

The sphingoid-polyalkylamine conjugate may also be combined with other active substances known to be used in combination with antigenic molecules. Such substances include, for example, immunostimulating agents (also known by the term "immunostimulant" or "adjuvant"). This includes any substance that when added to a vaccine it improves the immune response so that less vaccine is needed to produce a greater response. The immunostimulating agent may be provided together with the conjugate/biologically active material, or within a specified time interval (e.g. several hours or days before or after the administration of the conjugate/biologically active molecule).

Preferred immunostimulating agents include, without being limited thereto, cytokines, such as interleukins (L-2, IL-10, IL-12, IL-15, IL-18), interferons (IFN alpha, beta, gamma), oligodeoxynucleotides (ODN), toxins (e.g. cholera toxin (CT), staphylococcal enterotoxin B (SEB)) heat label *E. Coli* enerotoxin (HLT) as well as any other adjuvants known to be used in the art for enhancing or stimulating the immune response to an antigenic molecule.

The assemblies may include the sphingoid-polyalkylamine conjugate (non-methylated or methylated) as the sole lipid-like ingredient, or be combined with other helper lipid substances. Such helper lipid substances may include non-cationic lipids like DOPE, DOPC, DMPC, Cholesterol, oleic acid or others at different mole ratios to the lipid-like compound. Cholesterol is one preferred added substance for in vivo application while DOPE may be a preferred helper lipid for in vitro applications. In this particular embodiment the mole ratio of cholesterol to cationic lipid is within the range of 0.01-1.0 and preferably 0.1-0.4.

The assemblies may also include enhancers (as known in the art, such as $CaCl_2$ and soluble polyalkylamines.

Other components which may be included in the lipid assembly, and which are known to be used in structures of the like, are steric stabilizers. One example of a commonly used steric stabilizer is the family of lipopolymers, e.g. polyethylene glycol derivatized lipids (PEG-lipid conjugate). This family of compounds are know, inter alia, to increase (extend) the circulation time of lipids.

According to one embodiment, the formed liposomes may be shaped as unsized heterogeneous and heterolamellar vesicles (UHV) having a diameter of about 50-5000 nm. The formed UHV, may be downsized and converted to large (more homogenous) unilamellar vesicles (LUV) having a diameter of about 50-100 nm by further processing. The structure and dimensions of the vesicles, e.g. their shape and size may have important implications on their efficiency as vehicles for delivery of the active biological entities to the target, i.e. these determine their delivery properties.

A preferred group of polyalkylamine chains forming part of the sphingoid-polyalkylamine conjugate have been structurally defined hereinabove in connection with formula (I). According to this embodiment, the polyalkylamine chains, which may be the same or different in the conjugate of formula (I), are selected from spermine, spermidine, a polyalkylamine analog or a combination of same thereof. The term polyalkylamine analog is used to denote any polyalkylamine chain, and according to one embodiment denotes a polyalkylamine comprising 1 to 10 amine groups, preferably from 3- to 6 and more preferably 3 or 4 amine groups. Each alkylamine within the polyalkylamine chain may be the same or different and may be a primary, secondary, tertiary or quaternary amine.

The alkyl moiety, which may be the same or different within the polyalkylamine chain, is preferably a $C_1$-$C_6$ aliphatic repeating unit. Some non-limiting examples of polyalkylamine s include spermidine, N-(2-aminoethyl)-1,3-propane-diamine, 3,3'-iminobispropylamine, spermine and bis (ethyl) derivatives of spermine, polyethyleneimine.

The most preferred sphingoid-polyalkylamine conjugate according to the invention is N-palmitoyl D-erythro sphingosyl carbamoyl-spermine (CCS). This conjugate includes a ceramide linked via a carbamoyl bond to spermine.

The sphingoid-polyalkylamine conjugate according to the invention is preferably used for the preparation of a vaccine.

According to one embodiment, the sphingoid-polyalkylamine conjugate, and preferably the CCS, is used for the preparation of an influenza vaccine. In this particular embodiment, the biologically active material is derived from the influenza virus or a biologically active analog of a molecule derived from influenza virus. Such analogs include any substance which includes an influenza derived antigenic fragment which elicits an immune response.

A specific influenza derived antigenic material is the hemagglutinin (HA) and neuraminidase (NA) molecules, the combination is referred to as HN.

The present invention also concerns a method for modulating the immune response of a subject, the method comprises treating said subject with the sphingoid-polyalkylamine conjugate together with a biologically active material.

The combined treatment includes administration of the sphingoid-polyalkylamine conjugate and biologically active material either together, or within a predefined time interval, such as several hours or several days (optionally in combination with an immunostimulant). However, according to a preferred embodiment, the conjugate and biologically active material are mixed together prior to administration to the subject.

Administration of the sphingoid-polyalkylamine conjugate together with the biologically active material concerns another aspect of the invention. Accordingly, there is provided a pharmaceutical composition comprising a physiologically acceptable carrier and an effective amount of the sphingoid-polyalkylamine conjugate together with the biologically active material. The pharmaceutical composition optionally comprises an immunostimulant.

The sphingoid-polyalkylamine conjugated in combination with the biologically active material may be administered and dosed in accordance with good medical practice, taking into account the clinical condition of the individual patient, the site and method of administration, scheduling of administration, patient age, sex, body weight and other factors known to medical practitioners.

The "effective amount" for purposes herein denotes an amount which is effective to modulate (enhance or stimulate, as defined above) the subject's immune response relative to the effect obtained when the biologically active material is provide to the subject without the sphingoid-polyalkylamine conjugate. Preferably, the amount is effective to achieve effective immunization of a subject against a specific disease or disorder.

Notwithstanding the above, the amount may be effective to achieve suppression or inhibition of the immune response, e.g. for the purpose of treating allergy or autoimmune responses.

The composition of the invention comprising the sphingoid-polyalkylamine conjugate associated with the biologically active material may be administered in various ways: Non-limiting examples of administration routes include oral, subcutaneous (s.c.), parenteral including intravenous (i.v.), intra-arterial (i.a.), intramuscular (i.m.), intraperitoneal (i.p.)' intrarectal (i.r.) and intranasal (i.n.) administration, as well as by infusion techniques to the eye intraocular. Preferably modes of administration are the intranasal or intramuscular administrations.

The physiologically acceptable carrier according to the invention generally refers to inert, non-toxic solid or liquid substances preferably not reacting with the biologically active material or with the conjugate and which is required for the effective delivery of the conjugate with the biologically active molecule.

Non-limiting examples of physiologically acceptable carrier include water, saline, 5% dextrose (glucose), 10% sucrose etc., either alone or with minor amounts (up to 10%) of an alcohol, such as ethanol.

Preferably, the composition of the invention is a liquid formulation, including suspensions, aqueous solutions or in the form of an aerosol, all of which are known to those versed in the art. Aerosol formulations can be placed into pressurized acceptable propellants, such as propane, nitrogen, and the like. They also may be formulated as pharmaceuticals for non-pressured preparations, such as in a nebulizer or atomizersuitable carriers.

DESCRIPTION OF THE SPECIFIC EXAMPLES

Influenza

Characterization of HN Antigen-Loaded Cationic Liposomes

Efficiency of encapsulation of HN (a commercial preparation of hemagglutinin and neuraminidase derived from influenza viruses) loaded onto various cationic liposomal formulations, at different lipid/protein w/w ratios (3/1-300/1), and with or without cholesterol (Chol) was tested. Table 1 shows the results of such an experiment, using the cationic lipids DOTAP and CCS.

TABLE 1

The effect of the lipid (DOTAP, CCS)/protein ratio and cholesterol (Chol) on HN encapsulation efficiency

| DOTAP/ HN w/w ratio | DOTAP/ Chol mole ratio | % HN encapsu-lation | CCS/ HN w/w ratio | CCS/ Chol mole ratio | % HN encapsu-lation |
|---|---|---|---|---|---|
| 300/1 | 1/1 | 93 | 300/1 | 1/0 | 73 |
| 100/1 | 1/1 | 90 | 100/1 | 1/0 | 64 |
| 50/1 | 1/1 | 90 | 30/1 | 1/0 | 38 |
| 30/1 | 1/1 | 88 | 10/1 | 1/0 | 1 |
| 10/1 | 1/1 | 79 | | | |
| 3/1 | 1/1 | 35 | | | |
| 100/1 | 1/0 | 90 | 300/1 | 3/2 | 71 |
| 100/1 | 1/1 | 92 | 100/1 | 3/2 | 64 |
| 100/1 | 2/1 | 89 | 30/1 | 3/2 | 41 |
| 100/1 | 4/1 | 80 | 10/1 | 3/2 | 0 |

A monovalent vaccine was used for DOTAP and a trivalent vaccine for CCS.

The percentage of loading for DOTAP was 75-90% using a lipid/protein w/w ratio of 50/1 to 300/1, with and without Chol. At lipid/protein w/w ratios of 30/1 to 300/1, ~90% antigen loading was achieved, decreasing to 79% and 35% at 10/1 and 3/1 w/w ratios, respectively. The addition of Chol to the formulation did not affect loading at DOTAP/Chol mole ratios of 1/1 and 2/1, with slightly lower encapsulation (80%) at a ratio of 4/1. For CCS, with or without Chol, the loading efficiency was lower (64-73% at w/w ratio of 100/1-300/1).

HN association with the liposomes upon simple mixing of the soluble antigen with preformed empty liposomes was also determined. In such cases, 40-60% of the antigen was associated with the liposomes using a lipid/protein w/w ratio of 100/to 300/1, regardless of the formulation.

These finding, collectively, indicate very high loading efficiency (>60%) using a simple and fast (5 min.) procedure in all formulations. Furthermore, even preformed liposomes in aqueous suspension were capable of effectively associating with the influenza virus surface antigens.

The immunogenicity of the various lipid/antigen w/w ratios (with or without the addition of cholesterol) was also evaluated.

In a first experiment sera levels of HI, IgG1 and IgG2a antibodies following i.n. vaccination of young (2-month-old) BALB/c mice with HN-loaded neutral, anionic or cationic liposomes were determined (Table 2A). The HN antigen was a monovalent subunit vaccine derived from the A/New Caledonia (H1N1) strain. In the same experiment, lung and nasal levels of HI, IgG1, IgG2a and IgA antibodies, and INFγ levels produced by spleen cells, were also tested (Tables 2B and 2C).

TABLE 2A

Sera levels of HI, IgG1 and IgG2a antibodies

| Group (n = 5) | Vaccine | Serum HI (mean ± SD) | Serum IgG1 | Serum IgG2a |
|---|---|---|---|---|
| 1 | PBS | 0 | 0 | 0 |
| 2 | F-HN | 0 | 55 | 0 |
| 3 | Lip (DMPC)-HN (Neutral) | 3 ± 7 (0) | 150 | 0 |
| 4 | Lip (DMPC/DMPG)-HN (Anionic) | 6 ± 13 (20) | 500 | 0 |
| 5 | Lip (DC-Chol:DOPE)-HN | 18 ± 7 (0) | 0 | 0 |
| 6 | Lip (DSTAP:Chol)-HN | 28 ± 29 (40) | 20 | 0 |
| 7 | Lip (DDAB:Chol)-HN | 136 ± 32 (100) | 100 | 0 |
| 8 | Lip (DOTAP:Chol)-HN | 576 ± 128 (100) | 15000 | 730 |
| 9 | Lip (DMTAP:Chol)-HN | 672 ± 212 (100) | 30000 | 470 |
| 10 | Lip (CCS:Chol)-HN | 2368 ± 1805 (100) | 30000 | 9000 |
| 11 | F-HN + CT (1 μg) | 1664 ± 572 (100) | 55000 | 7000 |

F-HN, free antigen; Chol, cholesterol; CT, cholera toxin. Groups 5-10 are cationic liposomes. In parentheses, % seroconversion - % of mice with HI titer ≥ 40.

In particular, a comparison was made between neutral (DMPC), anionic (DMPC/DMPG, 9/1 mole ratio) and cationic (6 formulations) assemblies (Lip) encapsulating the HN antigens to induce local and systemic responses following two i.n. administrations. For all formulations, the lipid/HN w/w ratio was 300/1, and the cationic lipid/Chol or cationic lipid/DOPE mole ratio was 1/1. Free antigen (F-HN) and F-HN co-administered with cholera toxin (CT, 1 μg) as an adjuvant were tested in parallel. The vaccine was given on days 0 and 7, 3 μg/dose (10 μl per nostril), and the responses were determined 46 weeks after the second vaccine dose.

TABLE 2B lung and nasal wash levels of IgG1, IgG2a and IgA antibodies

| Group (n = 5) | Vaccine | Lung IgG1 | Lung IgG2a | Lung IgA | Nasal IgG1 | Nasal IgG2a | Nasal IgA |
|---|---|---|---|---|---|---|---|
| 1 | PBS | 0 | 0 | 0 | 0 | 0 | 0 |
| 2 | F-HN | 0 | 0 | 0 | 0 | 0 | 0 |
| 3 | Lip (DMPC)-HN (Neutral) | 30 | 0 | 0 | 0 | 0 | 0 |
| 4 | Lip (DMPC/DMPG)-HN (Anionic) | 40 | 0 | 0 | 0 | 0 | 0 |
| 5 | Lip (DC-Chol:DOPE)-HN | 0 | 0 | 0 | 0 | 0 | 0 |
| 6 | Lip (DSTAP:Chol)-HN | 0 | 20 | 0 | 0 | 80 | 0 |
| 7 | Lip (DDAB:Chol)-HN | 0 | 80 | 30 | 0 | 30 | 0 |
| 8 | Lip (DOTAP:Chol)-HN | 730 | 1050 | 170 | 40 | 180 | 30 |
| 9 | Lip (DMTAP:Chol)-HN | 470 | 3000 | 30 | 15 | 80 | 70 |
| 10 | Lip (CCS:Chol)-HN | 9000 | 30000 | 1900 | 15000 | 30 | 300 |
| 11 | F-HN + CT (1 μg) | 7000 | 10000 | 1800 | 40 | 120 | 30 |

TABLE 2C

Spleen INFγ levels (pg/ml)

| Group (n = 5) | Vaccine | Spleen IFNγ (pg/ml) |
|---|---|---|
| 1 | PBS | 1800 |
| 2 | F-HN | 1400 |
| 3 | Lip (DMPC)-HN (Neutral) | 4200 |
| 4 | Lip (DMPC/DMPG)-HN (Anionic) | 4000 |
| 5 | Lip (DC-Chol:DOPE)-HN | 4900 |
| 6 | Lip (DSTAP:Chol)-HN | 2300 |
| 7 | Lip (DDAB:Chol)-HN | 3100 |
| 8 | Lip (DOTAP:Chol)-HN | 8000 |
| 9 | Lip (DMTAP:Chol)-HN | 7800 |
| 10 | Lip (CCS:Chol)-HN | 10200 |
| 11 | F-HN + CT (1 μg) | 5200 |

As shown in Tables 2A-2C, the free antigen, as well as the neutral and anionic Lip-HN were virtually ineffective mucosal vaccines. In contrast, the cationic Lip-HN, particularly those designated DOTAP-HN, DMTAP-HN and CCS-HN evoked a robust systemic and mucosal humoral response, with high levels of IgG1, IgG2a and IgA antibodies, namely a mixed Th1+Th2 response. No IgE antibodies were defected. The cationic liposomal vaccines comprising DOTAP-HN, DMTAP-HN and CCS-HN also induced high levels of IFNγ (but not IL-4) in antigen-stimulated spleen cells. The responses produced by CCS-HN were even stronger than those induced by F-HN adjuvanted with CT. Based on these findings, only the cationic liposomal formulations: DOTAP-HN, DMTAP-HN and CCS-HN were further used.

In a second experiment, the effect of lipid/EN w/w ratio on the immunogenecity of HN-loaded cationic liposomes and of preformed liposomes simply mixed with the soluble antigen, was determined. The data shown in Tables 3A-3C indicate that all three formulations induced a strong systemic (serum) and local (lung) response, and that lowering the lipid/HN w/w ratio below 100/1 markedly reduced the response.

TABLE 3A

| Serum levels of HI, IgG1, IgG2a and IgA antibodies | | | | | | |
|---|---|---|---|---|---|---|
| No. | Vaccine (n = 5) | Lipid/HN w/w ratio | Serum HI | IgG1 | IgG2a | IgA |
| 1 | F-HN | | 0 | 0 | 0 | 0 |
| 2 | Lip (DOTAP)-HN | 300/1 | 496 ± 295 (100) | 15000 | 450 | 0 |
| 3 | | 100/1 | 196 ± 119 (100) | 5000 | 280 | 0 |
| 4 | | 30/1 | 36 ± 50 (80) | 1000 | 200 | 0 |
| 5 | | 10/1 | 28 ± 18 (60) | 600 | 30 | 0 |
| 6 | | 3/1 | 0 | 20 | 0 | 0 |
| 7 | Lip (DMTAP)-HN | 300/1 | 388 ± 260 (100) | 2500 | 250 | 0 |
| 8 | | 100/1 | 208 ± 107 (100) | 2200 | 600 | 0 |
| 9 | | 50/1 | 130 ± 118 (80) | 850 | 150 | 0 |
| 10 | | 30/1 | 48 ± 71 (40) | 450 | 0 | 0 |
| 11 | | 10/1 | 24 ± 35 (40) | 120 | 0 | 0 |
| 12 | Lip (CCS)-HN | 300/1 | 560 ± 480 (100) | 2000 | 1800 | 200 |
| 13 | | 100/1 | 752 ± 504 (100) | 6500 | 6000 | 0 |
| 14 | | 50/1 | 272 ± 156 (100) | 1900 | 700 | 0 |
| 15 | | 30/1 | 112 ± 125 (80) | 650 | 400 | 0 |
| 16 | | 10/1 | 52 ± 68 (40) | 275 | 440 | 0 |
| 17 | F-HN + CT (1 μg) | — | 896 ± 350 (100) | 30000 | 8000 | 120 |
| 18 | F-HN + Lip (DOTAP) | 300/1 | 864 ± 446 (100) | 5000 | 1500 | 0 |
| 19 | F-HN + Lip (DMTAP) | 300/1 | 320 ± 226 (100) | 1900 | 400 | 0 |
| 20 | F-HN + Lip (CCS) | 300/1 | 704 ± 525 (100) | 30000 | 5000 | 500 |

In groups 18-20 preformed liposomes were mixed with the soluble antigen.

TABLE 3B

| Lung levels of HI, IgG1, IgG2a and IgA | | | | | | |
|---|---|---|---|---|---|---|
| No. | Vaccine (n = 5) | Lipid/HN w/w ratio | Lung HI | IgG1 | IgG2a | IgA |
| 1 | F-HN | | 0 | 0 | 0 | 0 |
| 2 | Lip (DOTAP)-HN | 300/1 | 40 | 600 | 85 | 30 |
| 3 | | 100/1 | 40 | 500 | 20 | 0 |
| 4 | | 30/1 | 30 | 250 | 35 | 0 |
| 5 | | 10/1 | 20 | 250 | 0 | 0 |
| 6 | | 3/1 | 10 | 20 | 0 | 0 |
| 7 | Lip (DMTAP)-HN | 300/1 | 0 | 5500 | 200 | 1200 |
| 8 | | 100/1 | 0 | 7000 | 350 | 0 |
| 9 | | 50/1 | 0 | 4500 | 250 | 0 |
| 10 | | 30/1 | 0 | 1500 | 110 | 0 |
| 11 | | 10/1 | 0 | 500 | 0 | 0 |
| 12 | Lip (CCS)-HN | 300/1 | 80 | 12500 | 3000 | 20000 |
| 13 | | 100/1 | 80 | 7000 | 5500 | 65000 |
| 14 | | 50/1 | 40 | 5500 | 900 | 20000 |
| 15 | | 30/1 | 0 | 1500 | 200 | 0 |
| 16 | | 10/1 | 0 | 500 | 200 | 0 |
| 17 | F-HN + CT (1 μg) | — | 80 | 45000 | 2250 | 3000 |
| 18 | F-HN + Lip (DOTAP) | 300/1 | 0 | 6000 | 500 | 1200 |
| 19 | F-HN + Lip (DMTAP) | 300/1 | 0 | 3750 | 225 | 1500 |
| 20 | F-HN + Lip (CCS) | 300/1 | 80 | 35000 | 3000 | 80000 |

TABLE 3C

| Spleen INFγ levels (pg/ml) | | | |
|---|---|---|---|
| No. | Vaccine (n = 5) | Lipid/HN w/w ratio | Spleen IFNγ (pg/ml) |
| 1 | F-HN | | 7430 |
| 2 | Lip (DOTAP)-HN | 300/1 | 9780 |
| 3 | | 100/1 | 42220 |
| 4 | | 30/1 | 20440 |

TABLE 3C-continued

| Spleen INFγ levels (pg/ml) | | | |
|---|---|---|---|
| No. | Vaccine (n = 5) | Lipid/HN w/w ratio | Spleen IFNγ (pg/ml) |
| 5 | | 10/1 | 20400 |
| 6 | | 3/1 | 27780 |
| 7 | Lip (DMTAP)-HN | 300/1 | Not done |
| 8 | | 100/1 | |
| 9 | | 50/1 | |
| 10 | | 30/1 | |
| 11 | | 10/1 | |
| 12 | Lip (CCS)-HN | 300/1 | |
| 13 | | 100/1 | |
| 14 | | 50/1 | |
| 15 | | 30/1 | |
| 16 | | 10/1 | |
| 17 | F-HN + CT (1 μg) | — | |
| 18 | F-HN + Lip (DOTAP) | 300/1 | |
| 19 | F-HN + Lip (DMTAP) | 300/1 | |
| 20 | F-HN + Lip (CCS) | 300/1 | |

The superiority of Lip CCS-HN vaccine over the other vaccine formulations is again seen as reflected by the high levels of serum and lung IgG2a and IgA antibodies (groups 12-16). Interestingly, simple mixing of soluble antigen with preformed liposomes generated very potent vaccines (groups 18-20) that are equal to liposomes encapsulating the antigen. This suggests that real encapsulation of the antigen may not be necessary for the adjuvanticity of the cationic assemblies/liposomes.

In a further experiment the effect of cholesterol on the immunogenicity of the HN-loaded liposomes was tested. Tables 4A-4C show the results of this experiment, indicating that the addition of Chol slightly reduced the systemic HI response to DOTAP-HN at 2/1 and 4/1 mole ratios (groups 4, 5), but not at a 1/1 mole ratio (group 3), and moderately enhances the overall response to DMTAP-HN at all ratios (groups 7-9) and the local (lung) response CCS-HN at a 1/1 ratio (group 11).

TABLE 4A

Serum levels of HI, IgG1, IgG2a and IgA antibodies

| No. | Vaccine (n = 5) | Cat lipid/Chol w/w ratio | Serum HI | IgG1 | IgG2a | IgA |
|---|---|---|---|---|---|---|
| 1 | F-HN | — | 0 | 0 | 0 | 0 |
| 2 | Lip (DOTAP)-HN | 1/0 | 320 ± 0 (100) | 15000 | 450 | 0 |
| 3 | Lip (DOTAP:Chol)-HN | 1/1 | 496 ± 295 (100) | 15000 | 450 | 0 |
| 4 | | 2/1 | 168 ± 216 (100) | 7000 | 800 | 0 |
| 5 | | 4/1 | 195 ± 111 (100) | 15000 | 250 | 0 |
| 6 | Lip (DMTAP)-HN | 1/0 | 320 ± 188 (100) | 20000 | 290 | 0 |
| 7 | Lip (DMTAP:Chol)-HN | 1/1 | 672 ± 419 (100) | 30000 | 300 | 0 |
| 8 | | 2/1 | 576 ± 368 (100) | 25000 | 650 | 0 |
| 9 | | 4/1 | 608 ± 382 (100) | 30000 | 600 | 0 |
| 10 | Lip (CCS)-HN | 1/0 | 2560 ± 1568 (100) | 30000 | 7000 | 100 |
| 11 | Lip (CCS:Chol)-HN | 1/1 | 2368 ± 1805 (100) | 30000 | 9000 | 100 |
| 12 | F-HN + CT (1 μg) | — | 1664 ± 572 (100) | 55000 | 7000 | 20 |

TABLE 4B

Lung levels of HI, IgG1, IgG2a and IgA antibodies

| No. | No. Vaccine (n = 5) | Cat lipid/Chol w/w ratio | Lung HI | IgG1 | IgG2a | IgA |
|---|---|---|---|---|---|---|
| 1 | F-HN | — | 0 | 0 | 0 | 0 |
| 2 | Lip (DOTAP)-HN | 1/0 | 40 | 900 | 85 | 25 |
| 3 | Lip (DOTAP:Chol)-HN | 1/1 | 40 | 600 | 80 | 30 |
| 4 | | 2/1 | 40 | 680 | 180 | 22 |
| 5 | | 4/1 | 60 | 720 | 50 | 60 |
| 6 | Lip (DMTAP)-HN | 1/0 | 60 | 1000 | 40 | 0 |
| 7 | Lip (DMTAP:Chol)-HN | 1/1 | 120 | 3000 | 30 | 15 |
| 8 | | 2/1 | 160 | 2500 | 160 | 200 |
| 9 | | 4/1 | 80 | 4000 | 100 | 150 |
| 10 | Lip (CCS)-HN | 1/0 | 640 | 30000 | 1500 | 9000 |
| 11 | Lip (CCS:Chol)-HN | 3/2 | 1280 | 30000 | 1900 | 15000 |
| 12 | F-HN + CT (1 μg) | — | 20 | 10000 | 1800 | 1000 |

TABLE 4C

Spleen INFγ levels (pg/ml)

| No. | No. Vaccine (n = 5) | Cat lipid/Chol w/w ratio | Spleen IFNγ (pg/ml) |
|---|---|---|---|
| 1 | F-HN | — | 7430 |
| 2 | Lip (DOTAP)-HN | 1/0 | 7480 |
| 3 | Lip (DOTAP:Chol)-HN | 1/1 | 9780 |
| 4 | | 2/1 | 12870 |
| 5 | | 4/1 | 9330 |
| 6 | Lip (DMTAP)-HN | 1/0 | 8520 |
| 7 | Lip (DMTAP:Chol)-HN | 1/1 | 10900 |
| 8 | | 2/1 | 8560 |
| 9 | | 4/1 | 7490 |
| 10 | Lip (CCS)-HN | 1/0 | 15550 |
| 11 | Lip (CCS:Chol)-HN | 3/2 | 13780 |
| 12 | F-HN + CT (1 μg) | — | 11110 |

The immunogenicity of CCS-HN vaccine was also evaluated in aged (18 month) C57BL/6 mice following intramuscular (once on day 0) or intranasal (twice, days 0 and 7) administration of 1 μg and 2 μg, respectively, of subunit (HN) vaccine (derived from A/Panama [H3N2] virus). The lipid assemblies were composed of CCS/cholesterol (3:2 molar ratio) and the lipid/HN w/w ratio was 200:1. As opposed to zero activity of the commercial vaccine, the CCS-HN vaccine evoked high levels of serum HI and IgG2a antibodies (tested at 4 weeks post vaccination) and lung (tested at 6 weeks post vaccination) IgG2a and IgA antibodies as can be seen in Tables 5A and 5B (the data show mean titers).

TABLE 5A

Serum levels of HI, IgG1, IgG2a and IgA in aged mice

| No. | Vaccine[a] (n = 5) | Serum HI | IgG1 | IgG2a |
|---|---|---|---|---|
| 1 | PBS i.n. × 2 | 0 | 0 | 0 |
| 2 | F-HN i.m. × 1 | 0 | 15 | 0 |
| 3 | F-HN i.n. × 2 | 0 | 0 | 0 |
| 4 | Lip (CCS)-HN i.n. × 2 | 80 | 130 | 350 |

TABLE 5B

Lung levels of IgG1, IgG2a and IgA in aged mice

| No. | Vaccine (n = 5) | Lung IgG1 | IgG2a | IgA |
|---|---|---|---|---|
| 1 | PBS i.n. × 2 | 0 | 0 | 0 |
| 2 | F-HN i.m. × 1 | 0 | 0 | 0 |
| 3 | F-HN i.n. × 2 | 0 | 0 | 0 |
| 4 | CCS-HN i.n. × 2 | 0 | 180 | 840 |

In addition, the induction of cellular responses by the various vaccine formulations was tested. In particular, young mice were immunized i.n. with various cationic liposomal formulations and the splenocyte cellular responses—cytotoxicity, proliferation and IFNγ production—were measured 6 weeks after vaccination. In the experiment, the results of which are shown in Table 6, a comparison was made between HN-loaded liposomes (groups 3-10) and free antigen (F-HN) given alone (group 2) or admixed with preformed empty liposomes (groups 11-13). The immunogenicity of Lip (DMTAP)-HN and Lip (CCS)-HN prepared at varying lipid/HN w/w ratios (30/1-300/1) was also determined.

TABLE 6

Induction of cellular responses by cationic liposomes administered i.n.

| No. | Vaccine | Lipid/HN w/w ratio | % cytotoxicity P815 + peptide | % cytotoxicity P815 | Proliferation Δcpm (mean) | IFNγ (pg/ml) |
|---|---|---|---|---|---|---|
| 1 | PBS | — | 6 | 4 | 7010 | 1900 |
| 2 | F-HN | — | 8 | 5 | 7700 | 4500 |
| 3 | Lip (DMTAP)-HN | 300/1 | 16 | 13 | 10960 | 3500 |
| 4 | | 100/1 | 9 | 9 | 12870 | 5850 |
| 5 | | 50/1 | 3 | 2 | 17670 | 3400 |
| 6 | | 30/1 | 3 | 2 | 17920 | 3050 |
| 7 | Lip (CCS)-HN | 300/1 | 4 | 2 | 20370 | 8000 |
| 8 | | 100/1 | 21 | 7 | 24870 | 8250 |
| 9 | | 50/1 | 6 | 3 | 20980 | 10650 |
| 10 | | 30/1 | 8 | 5 | 11510 | 3500 |
| 11 | F-HN + Lip (DOTAP) | 300/1 | 17 | 4 | 19390 | 3400 |
| 12 | F-HN + Lip (DMTAP) | 300/1 | 17 | 7 | 11850 | 5700 |
| 13 | F-HN + Lip (CCS) | 300/1 | 16 | 8 | 19270 | 4100 |

Preferential cytotoxicity against the specific target cells (P815 pulsed with the influenza peptide) was obtained only with CCS-HN at a lipid/HN w/w ratio of 100/1 (group 8) and with all the three preformed liposomes (DOTAP, DMTAP and CCS) co-administered with free antigen. The maximum proliferative response was observed with DMTAP-HN at lipid/HN w/w ratios of 50/1 and 30/1 and with CCS-HN at 300/1, 100/1 and 50/1 ratios. The proliferative and cytotoxic responses elicited by the most efficacious liposomal formulations were 2-3 times greater than those induced by free antigen.

These findings suggest that as compared with the humoral response (Table 3), where the highest levels of all types of antibodies measured were obtained at lipid/HN w/w ratios of 100/1-300/1, lower w/w ratios (e.g. 30/1-100/1) may be optimal for the cellular responses. Moreover, whereas DMTAP-HN elicits a strong humoral response, this formulation is a poor inducer of cytotoxic activity, as compared with CCS-HN. Interestingly, vaccination with mixtures of free antigen with preformed cationic liposomes (all three formulations) in suspension evokes good cellular responses that are similar in magnitude to those induced by the encapsulated antigen. Thus, simple mixing of free antigen with preformed cationic liposomes may be sufficient to induce both strong humoral (Table 3A-3C) and cellular (Table 6) responses.

In yet a further experiment, the results of which are shown in Tables 7A-7C, a comparison was made between 1 i.m. dose, 1 or 2 i.n. doses and 2 oral doses of a monovalent HN-loaded cationic liposomes comprising DOTAP, DMTAP or CCS with regard to immunogenicity and induction of protective immunity to live virus challenge. In this experiment, the lipid/N w/w ratio was 300/1 and the cationic lipid/Chol ratio was 1/1 for DOTAP and DMTAP systems and 3/2 for CCS system. Of the three routes, i.n. administration twice generates the strongest humoral and cellular response and protective immunity. Of the 3 formulations, CCS induces the highest response, particularly with regard to IgG2a and IgA antibodies.

TABLE 7A

Serum levels of HI, IgG1, IgG2a and IgA

| No. | Vaccine (n = 10) | Route | HI | Serum IgG1 | Serum IgG2a | Serum IgA |
|---|---|---|---|---|---|---|
| 1 | PBS | | 0 | 0 | 0 | 0 |
| 2 | F-HN | i.m. × 1 | 60 ± 37 (70) | 1000 | 40 | 0 |
| 3 | | oral × 2 | 0 | 0 | 0 | 0 |
| 4 | | i.n. × 1 | 0 | 0 | 0 | 0 |
| 5 | | i.n. × 2 | 0 | 55 | 0 | 0 |
| 6 | Lip (DOTAP/Chol)-HN | i.m. × 1 | 424 ± 141 (100) | 21000 | 5500 | 0 |
| 7 | | oral × 2 | 0 | 0 | 0 | 0 |
| 8 | | i.n. × 1 | 40 ± 28 (50) | 450 | 80 | 0 |
| 9 | | i.n. × 2 | 409 ± 172 (100) | 25000 | 1300 | 60 |
| 10 | Lip (DMTAP/Chol)-HN | i.m. × 1 | 768 ± 211 (100) | 24000 | 8000 | 0 |
| 11 | | oral × 2 | 0 | 0 | 0 | 0 |
| 12 | | i.n. × 1 | 10 ± 10 (0) | 300 | 60 | 0 |
| 13 | | i.n. × 2 | 532 ± 763 (100) | 10500 | 380 | 50 |
| 14 | Lip (CCS/Chol)-HN | i.m. × 1 | 864 ± 1100 (100) | 25000 | 10000 | 0 |
| 15 | | oral × 2 | 0 | 0 | | |
| 16 | | i.n. × 1 | 34 ± 50 (20) | 1000 | 30 | 0 |
| 17 | | i.n. × 2 | 2289 ± 1576 (100) | 25000 | 20000 | 400 |
| 18 | F-HN + CT (1 μg) | i.n. × 2 | 756 ± 650 (100) | 21000 | 15000 | 20 |

TABLE 7B

| Lung antibodies | | | | | | |
|---|---|---|---|---|---|---|
| No. | Vaccine (n = 5) | Route | Lung HI | IgG1 | IgG2a | IgA |
| 1 | PBS | | 0 | 0 | 0 | 0 |
| 2 | F-HN | i.m. × 1 | 0 | 80 | 0 | 0 |
| 3 | | oral × 2 | 0 | 0 | 0 | 0 |
| 4 | | i.n. × 1 | 0 | 0 | 0 | 0 |
| 5 | | i.n. × 2 | 0 | 70 | 20 | 0 |
| 6 | Lip (DOTAP/Chol)-HN | i.m. × 1 | 40 | 900 | 500 | 0 |
| 7 | | oral × 2 | 0 | 0 | 0 | 0 |
| 8 | | i.n. × 1 | 0 | 50 | 20 | 0 |
| 9 | | i.n. × 2 | 120 | 10000 | 1000 | 350 |
| 10 | Lip (DMTAP/Chol)-HN | i.m. × 1 | 20 | 900 | 150 | 0 |
| 11 | | oral × 2 | 0 | 0 | 0 | 0 |
| 12 | | i.n. × 1 | 0 | 35 | 20 | 0 |
| 13 | | i.n. × 2 | 240 | 20000 | 700 | 2200 |
| 14 | Lip (CCS/Chol)-HN | i.m. × 1 | 60 | 3500 | 900 | 0 |
| 15 | | oral × 2 | 0 | 0 | 0 | 0 |
| 16 | | i.n. × 1 | 0 | 120 | 0 | 35 |
| 17 | | i.n. × 2 | 360 | 30000 | 5000 | 20000 |
| 18 | F-HN + CT (1 μg) | i.n. × 2 | 240 | 22000 | 2500 | 1800 |

TABLE 7C

| Cellular response and protective immunity | | | | | |
|---|---|---|---|---|---|
| No. | Vaccine (n = 5) | Route | Spleen Δcpm (mean) | IFNγ (pg/ml) | Lung Virus titer (log 10) |
| 1 | PBS | | 1641 | 0 | 7 |
| 2 | F-HN | i.m. × 1 | 1909 | 0 | 4 |
| 3 | | oral × 2 | 2253 | 0 | ND |
| 4 | | i.n. × 1 | 669 | 0 | ND |
| 5 | | i.n. × 2 | 2813 | 0 | 5 |
| 6 | Lip (DOTAP/Chol)-HN | i.m. × 1 | 3452 | 3300 | 0 |
| 7 | | oral × 2 | 0 | 1150 | ND |
| 8 | | i.n. × 1 | 482 | 1900 | ND |
| 9 | | i.n. × 2 | 8391 | 3200 | 0 |
| 10 | Lip (DMTAP/Chol)-HN | i.m. × 1 | 5632 | 0 | 1 |
| 11 | | oral × 2 | 553 | 0 | ND |
| 12 | | i.n. × 1 | 1277 | 0 | ND |
| 13 | | i.n. × 2 | 7331 | 3150 | 0 |
| 14 | Lip (CCS/Chol)-HN | i.m. × 1 | 6196 | 5750 | 0 |
| 15 | | oral × 2 | 476 | 550 | ND |
| 16 | | i.n. × 1 | 1705 | 6250 | ND |
| 17 | | i.n. × 2 | 4912 | 15500 | 0 |
| 18 | F-HN + CT (1 μg) | i.n. × 2 | 1933 | 5650 | 0 |

In the experiment described in Tables 8-10, a commercial trivalent vaccine was tested and a comparison was made between a single CCS-based vaccine dose (using 2 or 4 μg of antigen [HN] of each viral strain) and two vaccine doses (2 μg/strain/dose), given at 3, 7 or 14 day intervals between administrations. The lipid assemblies were composed of CCS/Chol (cholesterol) at a 3/2 mole ratio, and the lipid/HN w/w ratio was 100/1 for all formulations. As controls, the standard trivalent commercial vaccine (ES) was administered either alone or combined with 1 μg cholera toxin (CT), used as a mucosal adjuvant. Sera, lung homogenates and nasal washes were tested 5-6 weeks after the first vaccine dose for HI antibodies (Table 8), as well as for antigen-specific IgG1, IgG2a, IgA and IgE antibodies (Table 9). In addition, 5 mice from selected groups were challenged i.n. with live virus (using the mouse adapted reassortant X-127 virus) and protection was assessed by quantifying lung virus titer 4 days later (Table 10).

As opposed to the poor or no immunogenicity of the commercial flu vaccine (HN) (groups 2-6), CCS/Chol-flu vaccine induced high titers of all types of antibodies tested (except for IgE which was undetected), especially against the two A virus strains (groups 8-11; Tables 8, 9). For the 2-dose regimen, a 1-week interval appears to be the optimal (gr. 10). For the single dose regimen, 4 μg antigen, but not 2 μg (gr. 8 vs. gr. 7), induced high titers of serum HI, IgG1 and IgG2a antibodies and lung IgG1 antibodies. However, in comparison with the 2-dose regimen, the 1-dose regimen did not elicit lung IgG2a and IgA antibodies nor nasal antibodies (Table 9).

In the protection assay (Table 10), the CCS-flu vaccine administered i.n. either once (4 μg) or twice (2 μg/dose) afforded full protection against viral infection (6 log reduction in lung virus titer) whereas the standard vaccine reduced virus titer by only 0.5-1 log. Thus, although the single dose regimen with the CCS-flu vaccine is inferior to the two-dose regimen for certain antibody isotypes, the two regimens provide a similar degree of protection.

In this experiment, we also compared CCS alone to CCS/Chol as the vaccine carrier, and found no difference in immunogenicity between the two formulations (data not shown). Another formulation modification was the reduction of the size of the CCS/Chol lipid assemblies (diameter 0.05-5 μm) by extrusion (diameter≤0.02 μm). Antibody titers induced by the extruded vaccine were 50-80% lower than those produced by the non-extruded vaccine (data not shown). Thus, unsized CCS lipid assemblies, with or without cholesterol, are highly efficient as a vaccine carrier for trivalent flu vaccine.

TABLE 8

Elicitation of hemagglutination inhibition (HI) antibodies following intranasal vaccination with trivalent influenza vaccine, free and in CCS lipid assemblies, administered once or twice at various time intervals to young (2 mo.) BALB/C mice

| | | | | Mean HI titer (% seroconversion)[b] | | | | | |
|---|---|---|---|---|---|---|---|---|---|
| | | | Dosing | A/New Caledonia | | A/Panama | | B/Yamanashi | |
| No. | Vaccine[a] (n = 5) | | days | serum | lung | serum | lung | serum | lung |
| 1 | None (PBS) | ×2 | 0, 7 | 0 | 0 | 0 | 0 | 0 | 0 |
| 2 | F-HN | 2 μg × 1 | 0 | 0 | 0 | 0 | 0 | 0 | 0 |
| 3 | | 4 μg × 1 | 0 | 0 | 0 | 0 | 0 | 0 | 0 |
| 4 | | 2 μg × 2 | 0, 3 | 0 | 0 | 0 | 0 | 0 | 0 |

TABLE 8-continued

Elicitation of hemagglutination inhibition (HI) antibodies following intranasal vaccination with trivalent influenza vaccine, free and in CCS lipid assemblies, administered once or twice at various time intervals to young (2 mo.) BALB/C mice

| | | | | Mean HI titer (% seroconversion)[b] | | | | | |
|---|---|---|---|---|---|---|---|---|---|
| | | | Dosing | A/New Caledonia | | A/Panama | | B/Yamanashi | |
| No. | Vaccine[a] (n = 5) | | days | serum | lung | serum | lung | serum | lung |
| 5 | | 2 μg × 2 | 0, 7 | 0 | 0 | 0 | 0 | 0 | 0 |
| 6 | | 2 μg × 2 | 0, 14 | 0 | 0 | 0 | 0 | 0 | 0 |
| 7 | Lip (CCS/Chol)-HN | 2 μg × 1 | 0 | 0 | 0 | 0 | 0 | 0 | 0 |
| 8 | | 4 μg × 1 | 0 | 336 (100) | 40 | 328 (100) | 40 | 52 (80) | 0 |
| 9 | | 2 μg × 2 | 0, 3 | 544 (100) | 80 | 408 (100) | 40 | 52 (80) | 0 |
| 10 | | 2 μg × 2 | 0, 7 | 544 (100) | 80 | 544 (100) | 120 | 88 (100) | 0 |
| 11 | | 2 μg × 2 | 0, 14 | 480 (100) | 60 | 368 (100) | 40 | 80 (80) | 0 |
| 12 | F-HN + CT (1 μg) | 2 μg × 2 | 0, 7 | 608 (100) | 80 | 664 (100) | 120 | 84 (80) | 0 |

[a]Mice were immunized with Fluvirin ® 2003/2004 trivalent subunit vaccine preparation consisting of A/New Caledonia/20/99 (H1N1)-like, A/Moscow/10/99 (H3N2)-like and B/Hong Kong/330/2001-like, either free (F-HN) or incorporated into CCS/Chol (3/2 mole ratio) lipid assemblies (0.6 mg for groups 7, 9, 10, 11; 1.2 mg for group 8).
[b]Serum HI titer was determined on individual mice 35 days after the first vaccine dose. Lung (pooled) HI titer was tested on day 42. In parentheses - % of mice with HI titer ≥40. 0 denotes HI titer <20.

TABLE 9

Elicitation of serum, lung and nasal antigen-specific IgG1, IgG2a and IgA antibodies following intranasal vaccination with trivalent influenza vaccine, free and in CCS lipid assemblies, administered once or twice at various intervals to young (2 mo.) BALB/c mice

| | | | | Mean antibody titer | | | | | | | |
|---|---|---|---|---|---|---|---|---|---|---|---|
| | | | Dosing | Serum | | Lung Homogenate | | | Nasal wash | | |
| No. | Vaccine[a] (n = 5) | | days | IgG1 | IgG2a | IgG1 | IgG2a | IgA | IgG1 | IgG2a | IgA |
| 1 | None (PBS) | ×2 | 0, 7 | 0 | 0 | 0 | 0 | 0 | 0 | 0 | 0 |
| 2 | F-HN | 2 μg × 1 | 0 | 0 | 0 | 0 | 0 | 0 | 0 | 0 | 0 |
| 3 | | 4 μg × 1 | 0 | 320 | 90 | 1500 | 0 | 0 | 0 | 0 | 0 |
| 4 | | 2 μg × 2 | 0, 3 | 0 | 0 | 0 | 0 | 0 | 0 | 0 | 0 |
| 5 | | 2 μg × 2 | 0, 7 | 0 | 0 | 0 | 0 | 0 | 0 | 0 | 0 |
| 6 | | 2 μg × 2 | 0, 14 | 40 | 0 | 0 | 0 | 0 | 0 | 0 | 0 |
| 7 | Lip (CCS/Chol)-HN | 2 μg × 1 | 0 | 300 | 0 | 600 | 0 | 0 | 0 | 0 | 0 |
| 8 | | 4 μg × 1 | 0 | 12000 | 4500 | 13000 | 0 | 0 | 0 | 0 | 0 |
| 9 | | 2 μg × 2 | 0, 3 | 15000 | 10000 | 15000 | 2500 | 3500 | 0 | 10 | 0 |
| 10 | | 2 μg × 2 | 0, 7 | 15000 | 12000 | 14000 | 2500 | 9000 | 200 | 30 | 100 |
| 11 | | 2 μg × 2 | 0, 14 | 13000 | 5500 | 12000 | 1800 | 3000 | 50 | 0 | 0 |
| 12 | F-HN + CT (1 μg) | 2 μg × 2 | 0, 7 | 21000 | 15000 | 20000 | 2500 | 2000 | 250 | 30 | 45 |

[a]See table 8 for experimental details. Samples were pooled and tested by ELISA against the 3 viral strains (pooled HN) 42 days after the first vaccine dose. 0 denotes titer <10.

TABLE 10

Protection of young BALB/c mice against viral challenge following intranasal vaccination with trivalent influenza vaccine, free and in CCS lipid assemblies

| No. | Vaccine[a] (n = 5) | Dosing days | Lung virus titer (log 10)[b] |
|---|---|---|---|
| 1 | None | — | 6 |
| 2 | F-HN 4 μg × 1 | 0 | 5.5 |
| 3 | F-HN 2 μg × 2 | 0, 7 | 5 |
| 4 | Lip (CCS/Chol)-HN 4 μg × 1 | 0 | 0 |
| 5 | Lip (CCS/Chol)-HN 2 μg × 2 | 0, 7 | 0 |
| 6 | F-HN 2 μg + CT (1 μg) × 2 | 0, 7 | 0 |

[a]See table 8 for experimental details. In groups 4, 5 the lipid/HN w/w ratio was 100/1.
[b]The mice were infected intranasally 42 days after the first vaccine dose, using $\sim 10^6$ egg infectious dose 50% (EID 50) of the mouse-adapted reassortant X-127 virus (A/Beijing/262/95 [H1N1] × X-31 [A/Hong Kong/1/68 × A/PR/8/34). Lungs were harvested 4 days later, homogenized, serially diluted, and injected into the allantoic sac of 10 d. fertilized chicken eggs. After 48 h at 37° C. and 16 h at 4° C., 0.1 mL of allantoic fluid was removed and checked for viral presence by hemagglutination.

In the experiment described in Tables 11 and 12, the trivalent-flu vaccine was formulated with the CCS/Chol lipid assemblies using varying amounts of the HN antigens and the lipid. In this experiment the vaccines were prepared with: (a) varying amounts of the antigen (0.25-2 μg per viral strain) and of the lipid (0.075-0.6 mg), keeping the lipid/HN w/w ratio constant at 100/1; (b) graded amounts of the antigen (0.25-2 μg) and a constant amount of the lipid (0.6 mg) thereby varying the lipid/HN w/w ratio from 100/1 to 800/1. As can be seen in Table 11 (HI titer) and Table 12 (isotype titers) vaccines prepared at a 100/1 lipid/HN w/w ratio using 2 or 1 μg antigen of each strain and 0.6 or 0.3 mg lipid, respectively, produced high and similar levels of antibodies against the 3 viral strains (groups 2, 3). At lower antigen (0.5, 0.25 μg/strain) and lipid (0.15, 0.075 mg) doses the response decreased markedly (groups 4, 5), particularly the mucosal response (lung, nasal) (Table 12). When a constant dose of lipid was used (0.6 mg), high levels of antibodies were obtained even with the two lower doses of antigen (0.25, 0.5 μg/strain) (groups 6-8). Thus, the amount of the CCS lipid is critical, and with the appropriate lipid dose the antigen dose can be reduced 4-8 fold (from 1-2 μg to 0.25-0.5 μg).

TABLE 11

Effect of the antigen dose and lipid dose on the induction of HI antibodies following intranasal vaccination with trivalent influenza vaccine formulated with CCS lipid assemblies, administered twice (at 1 week interval) to young (2 mo.) BALB/c mice

| | | | | | Mean HI titer (% seroconversion) | | | | | |
|---|---|---|---|---|---|---|---|---|---|---|
| | | HN | Lipid | Lipid/HN | A/New Caledonia | | A/Panama | | B/Yamanashi | |
| No. | Vaccine[a] (n = 5) | (µg) | (mg) | w/w ratio | Serum | Lung | Serum | Lung | Serum | Lung |
| 1 | F-HN | 2 | — | — | 0 | 0 | 0 | 0 | 0 | 0 |
| 2 | Lip (CCS/Chol)-HN | 2 | 0.6 | 100/1 | 544 (100) | 80 | 544 (100) | 120 | 88 (100) | 0 |
| 3 | | 1 | 0.3 | 100/1 | 320 (100) | 80 | 544 (100) | 160 | 40 (100) | 0 |
| 4 | | 0.5 | 0.15 | 100/1 | 416 (100) | 20 | 448 (100) | 40 | 32 (100) | 0 |
| 5 | | 0.25 | 0.075 | 100/1 | 180 (100) | 0 | 100 (100) | 20 | 0 | 0 |
| 6 | | 1 | 0.6 | 200/1 | 672 (100) | 80 | 736 (100) | 160 | 104 (100) | 0 |
| 7 | | 0.5 | 0.6 | 400/1 | 560 (100) | 80 | 608 (100 | 160 | 104 (100) | 0 |
| 8 | | 0.25 | 0.6 | 800/1 | 512 (100) | 80 | 512 (100) | 120 | 48 (100) | 0 |

[a]See Table 8 for experimental details.

TABLE 12

Effect of the antigen dose and lipid dose on the induction of serum, lung and nasal antigen-specific IgG1, IgG2a and IgA antibodies following intranasal vaccination with trivalent influenza vaccine formulated with CCS lipid assemblies, administered twice (at 1 week interval) to young BALB/c mice

| | | | | | Mean antibody titer | | | | | | | |
|---|---|---|---|---|---|---|---|---|---|---|---|---|
| | | HN | Lipid | Lipid/HN | Serum | | Lung homogenate | | | Nasal wash | | |
| | Vaccine[a] (n = 5) | (µg) | (mg) | w/w ratio | IgG1 | IgG2a | IgG1 | IgG2a | IgA | IgG1 | IgG2a | IgA |
| 1 | F-HN | 2 | — | — | 0 | 0 | 0 | 0 | 0 | 0 | 0 | 0 |
| 2 | Lip (CCS/Chol)-HN | 2 | 0.6 | 100/1 | 15000 | 12000 | 14000 | 2500 | 9000 | 200 | 30 | 100 |
| 3 | | 1 | 0.3 | 100/1 | 14000 | 2500 | 10000 | 1000 | 8000 | 100 | 0 | 80 |
| 4 | | 0.5 | 0.15 | 100/1 | 15000 | 1300 | 8000 | 1500 | 4000 | 0 | 0 | 0 |
| 5 | | 0.25 | 0.075 | 100/1 | 12000 | 400 | 3500 | 400 | 2500 | 0 | 0 | 0 |
| 6 | | 1 | 0.6 | 200/1 | 20000 | 15000 | 12000 | 2500 | 8000 | 200 | 15 | 80 |
| 7 | | 0.5 | 0.6 | 400/1 | 15000 | 14000 | 15000 | 5000 | 15000 | 150 | 35 | 100 |
| 8 | | 0.25 | 0.6 | 800/1 | 15000 | 9000 | 21000 | 2500 | 13000 | 250 | 25 | 90 |

[a]See Tables 8, 9 for experimental details.

In a further experiment, the subunit flu vaccine, either free (HN) or associated with the CCS/Chol lipid assemblies (Lip HN), was tested for its ability to induce HI antibodies cross-reacting with various influenza A and B substrains that were not included in the vaccine. The data shown in Table 13 indicate that intranasal (i.n.) and intramuscular (i.m.) vaccination, administered once or twice, with either a monovalent or trivalent CCS-based influenza vaccine elicits high serum titers of HI antibodies directed against the immunizing strains, as well as HI antibodies cross-reacting with several A/H1N1, A/H3N2 and B strains that were circulating in the years 1986-1999 and were not included in the vaccine. Slightly lower HI titer were found after a single i.n. vaccine dose (gr. 6 vs. gr. 7). Lung homogenate HI titers (gr. 4, 8) were lower than the corresponding serum titers. Thus, parenteral or intranasal vaccination with the CCS-based vaccine may afford protection against a wide spectrum of A and B viral strains. Such antigenic variants may emerge during a flu epidemic/pandemic as a result of antigenic drift. In contrast, the standard commercial vaccine administered i.n. (gr. 1, 5) was totally ineffective in inducing antibodies against both the homologous and the heterologous strains.

TABLE 13

Induction of strain cross-reactive HI antibodies following intranasal or intramuscular vaccination of young BALB/c mice with CCS-based monovalent and trivalent influenza vaccine

| | | | | Mean HI titer against: | | | | | | | | | |
|---|---|---|---|---|---|---|---|---|---|---|---|---|---|
| | | | | A/H1N1 | | | | A/H3N2 | | | | B | |
| No. | Vaccine[a] | Vaccine strains | Sample tested | **New Caledonia/ 20/99** | Beijing/ 262/95 | Texas/ 36/91 | Singapore/ 6/86 | **Panama/ 2007/99** | Sydney/ 5/97 | Nanchang/ 333/95 | Johannesburg/ 33/94 | Yamanashi/ 166/98 | Harbin/ 07/94 |
| 1 | HN 2 µg × 2 i.n. | A/New Caledonia | serum | **0** | 0 | 0 | 0 | **0** | 0 | 0 | 0 | 0 | 0 |
| 2 | Lip HN 2 µg × 2 i.n. | | serum | **1280** | 1280 | 1280 | 240 | **0** | 0 | 0 | 0 | 0 | 0 |

TABLE 13-continued

Induction of strain cross-reactive HI antibodies following intranasal or intramuscular vaccination of young BALB/c mice with CCS-based monovalent and trivalent influenza vaccine

| | | | | Mean HI titer against: | | | | | | | | | |
|---|---|---|---|---|---|---|---|---|---|---|---|---|---|
| | | | | A/H1N1 | | | | A/H3N2 | | | | B | |
| No. | Vaccine[a] | Vaccine strains | Sample tested | **New Caledonia/ 20/99** | Beijing/ 262/95 | Texas/ 36/91 | Singapore/ 6/86 | **Panama/ 2007/99** | Sydney/ 5/97 | Nanchang/ 333/95 | Johannesburg/ 33/94 | Yamanashi/ 166/98 | Harbin/ 07/94 |
| 3 | Lip HN 1 μg × 1 i.m. | | serum | **640** | 640 | 320 | 40 | **0** | 0 | 0 | 0 | 0 | 0 |
| 4 | Lip HN 2 μg × 2 i.n. | | lung homogenate | **320** | 240 | 240 | 20 | **0** | 0 | 0 | 0 | 0 | 0 |
| 5 | HN 2 μg × 2 i.n. | A/New Caledonia, | serum | **0** | 0 | 0 | 0 | **0** | 0 | 0 | 0 | 0 | 0 |
| 6 | Lip HN 4 μg × 1 i.n. | A/Panama, B/Hong | serum | **320** | 80 | 120 | 0 | **320** | 320 | 120 | 120 | 60 | 120 |
| 7 | Lip HN 2 μg × 2 i.n. | Kong | serum | **480** | 120 | 240 | 20 | **640** | 640 | 120 | 120 | 80 | 320 |
| 8 | Lip HN 2 μg × 2 i.n. | | lung homogenate | **80** | 80 | 40 | 0 | **120** | 80 | 0 | 0 | 0 | 40 |
| 9 | HN 2 μg + CT 1 μg × 2 i.n. | | serum | **480** | 240 | 120 | 40 | **480** | 480 | 120 | 120 | 80 | 240 |

[a]Pooled sera and lung homogenate obtained 5 weeks after vaccination were tested for HI antibodies. For experimental details, see Table 8. The lipid (Lip) assemblies were composed of CCS/Chol (3/2 mole ratio) and the lipid/HN w/w ratio was 300/1 in groups 2-4 and 100/1 in groups 6-8. Except for groups 3 and 6, the two vaccine doses were spaced 1 week apart. In bold, antibody titers against the immunizing strains. 0 denotes HI titer <10.

Biodistribution of Anionic and Cationic Liposomes Loaded with HN and Administered Intranasally In a biodistribution experiment, 3 formulations of lipid assemblies: DMPC/DMPG (anionic), DOTAP/Chol (cationic) and CCS/Chol (cationic), either empty or loaded with the influenza HN antigens, were administered intranasally (200 μg lipid, 2 μg antigen per mouse) into BALB/c mice. The fluorescently labeled lipid was then traced in the homogenates of various tissues over a period of 24 h (at 1, 5, and 24 hours post administration).

As can be seen in the following Table 14 and in FIG. 2A-2F, after 1 and 5 hours there was 75-100% recovery of the administered lipid of all the three formulations tested. This recovery however dropped significantly at 24 hours in all formulations except for the CCS formulation. The CCS formulation containing the HN antigens displayed the longest retention (>24 h.) in the 3 target organs (nose, lungs, GI tract) while there was no lipid accumulation in the brain and no significant accumulation in the other organs tested (liver, kidneys, heart, spleen).

TABLE 14

Recovery at 1, 5, and 24 hours of fluorescently labeled lipid assemblies administered intranasal

| | % Recovery (of total lipid administered) | | |
|---|---|---|---|
| Lipid assembly formulation | 1 hour | 5 hours | 24 hours |
| DMPC/DMPG (empty) | 100.2 | 99.3 | 26.9 |
| DMPC/DMPG:HN | 100.2 | 99.9 | 8.3 |
| DOTAP/Chol (empty) | 107.0 | 75.1 | 8.1 |
| DOTAP/Chol:HN | 99.9 | 106.4 | 6.7 |
| CCS/Chol (empty) | 99.6 | 96.9 | 74.2 |
| CCS/Chol:HN | 101.1 | 101.5 | 94.5 |

When $^{125}$I-labeled HN was used, its biodistribution resembled that of the fluorescent lipid (data not shown). This long retention of the CCS vaccine components in the respiratory and GI tracts may explain, in part, its superior immunogenicity over the other liposomal formulations. This is exhibited in the following study in which the antigen component of the vaccine was traced. HN proteins were labeled with $^{125}$I and administered intranasally either free or associated with one of the lipid formulations used in the fluorescent biodistribution experiments. Radioactivity of the various tissues was determined at 1, 5 and 24 h post instillation.

Table 15 teaches that recovery of the antigen was high in this experiment as well. As can be seen in FIG. 3A-3D, the biodistribution pattern of the $^{125}$I-labeled HN is similar to that of the lipid (FIG. 2A-2F), further establishing that: (a) there is indeed an in vivo association between the HN-proteins and the lipid assemblies, and (b) the prolonged retention in the nose of the antigen when associated with the cationic lipid assemblies may be due to the cationic lipid assemblies and not an inherent property of the HN proteins, since there is no HN retention when the protein is administered by itself in soluble form.

Also this experiment may teach that there is no HN protein accumulation in the brain when administered alone or associated with lipid-assemblies (a major safety concern with intranasal vaccination). Since the radioactive tracing method is much more sensitive than the fluorescent method, this result is more confidently based.

TABLE 15

Recovery of $^{125}$I labeled HN administered intranasally either alone or associated with lipid assemblies at 1, 5 and 24 hours

| | Recovery (% of total injected) | | |
|---|---|---|---|
| Lipid assembly formulation | 1 hour | 5 hours | 24 hours |
| HN | 77 | 48 | 17 |
| Lip (DMPC:DMPG) HN | 88 | 50 | 26 |
| Lip (DOTAP:Chol) HN | 105 | 58 | 32 |
| Lip (CCS:Chol) HN | 100 | 74 | 41 |

In an attempt to test if the protein and lipid are retained and/or cleared by similar or different kinetics in the various tissues, another analysis of the data was performed, where the ratio between the % antigen retention (of the total dose administered) and % lipid retention in the various tissues at various time points was determined. When the ratio is constant and ≈1, it means that both components were similarly retained in the same organ, while when this ratio is either larger or smaller than 1 it suggests that the clearance kinetics of each component was different, and one component was cleared faster than the other.

As can be seen in Table 16 below, the only ratio that remained constant with time was that of CCS/Chol-HN in the nose (ratio=~0.45). This suggests that: (a) the high retention of the antigen in the nose with CCS and DOTAP is in correlation with the level of association and due to the binding of these formulations to the nasal mucosa, in contrast to DMPC/DMPG; and (b) while the other formulations' components dissociate in the body and are cleared at different rates, the CCS-HN based formulation was stable, especially in the nose, and this may contribute to the enhanced immunogenicity seen with the CCS-based vaccines.

TABLE 16

Retention of the lipid and HN antigen after i.n. administration

| | | Lip (DMPC:DMPG) HN | | | Lip (DOTAP:Chol) HN | | | Lip (CCS:Chol) HN | | |
|---|---|---|---|---|---|---|---|---|---|---|
| | | 1 h | 5 h | 24 h | 1 h | 5 h | 24 h | 1 h | 5 h | 24 h |
| HN | nose | 9% | 4% | 2% | 38% | 16% | 2% | 41% | 14% | 12% |
| | lungs | 30% | 3% | 4% | 19% | 4% | 12% | 24% | 21% | 11% |
| | GI | 35% | 32% | 11% | 33% | 27% | 10% | 22% | 28% | 8% |
| | recovery: | 88% | 50% | 26% | 105% | 58% | 32% | 100% | 74% | 41% |
| lipid | nose | 0% | 0% | 0% | 46% | 56% | 0% | 88% | 30% | 25% |
| | lungs | 67% | 80% | 5% | 38% | 3% | 3% | 12% | 35% | 14% |
| | GI | 33% | 20% | 4% | 16% | 47% | 3% | 1% | 37% | 55% |
| | recovery: | 100% | 100% | 8% | 100% | 106% | 7% | 101% | 102% | 95% |
| HN/lipid | nose | — | — | — | 0.82 | 0.29 | — | 0.47 | 0.45 | 0.47 |
| ratio | lungs | 0.44 | 0.03 | 0.85 | 0.50 | 1.29 | 3.56 | 2.01 | 0.60 | 0.80 |
| | GI | 1.07 | 1.56 | 2.96 | 2.12 | 0.57 | 2.86 | 16.08 | 0.76 | 0.15 |
| | recovery: | 0.88 | 0.50 | 3.12 | 1.05 | 0.55 | 4.78 | 0.99 | 0.73 | 0.44 |

The values show % retention of the total lipid or HN protein administered.

Preliminary Safety Study of the Intranasal Flu Vaccine

Toxicity (local, systemic) is a major concern with both i.m. and i.n. vaccines and therefore a pilot toxicity study was studied. Cationic lipid formulations (DMTAP, DOTAP, CCS-based) loaded with the influenza antigens hemagglutinin+neuraminidase (HN) were administered i.n. (twice, spaced 1 week apart) to mice (n=4/group), and blood counts (total, differential), blood chemistry and histological examination (nose, lung sections) were performed 72 hours later. The mice showed no apparent signs of any toxicity. Blood counts and blood chemistry were within the normal range, and, as expected, minimal-mild inflammatory response was seen in the nose and lungs of mice treated with the cationic formulations. A similar, albeit less pronounced, inflammatory response was also seen in some mice treated with saline alone or with the non-encapsulated antigen.

Immunomodulatory Activity of CCS-Flu Vaccine in Mice

In these experiments, mice were injected i.p. with various liposomal formulations (composed of DMPC, DMPC/DMPG, DOTAP/Chol, CCS/Chol), 0.5-1 mg lipid, with or without the HN antigens. The mice were either untreated or i.p. injected with thioglycollate (TG, to increase macrophage production) 2 days before the injection of the liposomal formulations. Peritoneal cells were harvested 24-48 h. after administration of the liposomes and used as such or after 4 h. adsorption at 37° C. to plastic dishes and removal of the non-adherent cells. In other experiments, peritoneal cells were harvested from TG treated mice and incubated with the liposomal formulations for 24-48 h. The cells were tested by flow cytometery for the expression of MHC II and the co-stimulatory molecules CD40 and B7. The supernatants were tested for the cytokines interferon γ (IFN γ), tumor necrosis factor α (TNF α) and interleukin 12 (IL-12), and for nitric oxide (NO).

All the cationic formulations (CCS/Chol, DOTAP/Chol, DMTAP/Chol) upregulated the expression of B7 and CD40 more than the other formulations (DMPC [neutral], DMPC/DMPG [anionic]) and induced higher levels of IFN γ and IL-12. In some cases the CCS/Chol formulation was more effective than the other cationic formulations. No significant levels of TNF α and NO were induced by any of the formulations. The enhanced expression of co-stimulatory molecules on antigen presenting cells and the induction of IL-12 and IFNγ by the cationic formulations can explain, in part, the greater adjuvant activity of these formulations. These findings combined with the long retention of the CCS-flu vaccine in the respiratory tract (FIGS. 2C and 2F and FIG. 3A-3D) after intranasal administration may explain why CCS is such an efficient mucosal vaccine carrier/adjuvant.

Hepatitis A Virus (HAV)

In addition to influenza, the immune enhancing potential of CCS lipid assemblies was also tested for HAV vaccine administered by the intranasal (i.n.) and the intrarectal (i.r.) routes.

HAV vaccine (Aventis Pasteur), 10 EU (~1.5 μg protein), was administered twice at a 2-week interval and the response was tested by the ELISPOT technique 3 weeks after the second vaccine dose. CpG-ODN, used as a mucosal adjuvant, was given at 10 μg/dose. The HAV-CCS lipid assemblies were prepared as described above for the influenza vaccine (Table 1).

The data presented in Table 17 show that whereas the commercial HAV vaccine failed to induce an IgA response in both tissues (lamina propria, Peyer's patches) tested, and by both administration routes (i.n., i.r.), the vaccine formulated with either CCS or CpG-ODN generated a significant response in most cases. The combination of HAV-CCS lipid assemblies and CpG-ODN resulted in a synergistic response in all cases. Thus, CCS lipid assemblies alone, and particularly in combination with CpG-ODN, are also effective as a carrier/adjuvant for mucosal vaccination against HAV.

TABLE 17

Induction of IgA antibodies following intranasal (i.n.) or intrarectal (i.r.) vaccination of BALB/c mice with hepatitis A virus (HAV) vaccine, alone and in combination with CCS lipid assemblies and/or CpG-ODN

| | Mean no. of IgA AFC/$10^6$ cells in: | | | |
|---|---|---|---|---|
| | Lamina propria | | Peyer's patches | |
| Vaccine | i.n. | i.r. | i.n. | i.r. |
| HAV alone | 0 | 0 | 0 | 0 |
| HAV-CCS | 12 | 27 | 0 | 1 |
| HAV + CpG-ODN | 16 | 22 | 0 | 14 |
| HAV-CCS + CpG-ODN | 139 | 68 | 28 | 23 |

AFC—antibody-forming-cells

*C. Botulinum*

In a further experiment, Mice were immunized i.n. with 0.4 μg dose of a commercial *C. botulinum* toxoid (as a model for bioterror agent, Uruguay, alum free) and antibody titers were tested by ELISA 4 weeks after the second vaccine dose.

The results of an experiment with *C. botulinum* toxoid are summarized in Table 18, which shows the superiority of the CCS-toxoid formulation over the standard vaccine following i.n. instillation, particularly with regard to the IgA levels in the small intestine and feces. Such Abs are expected to neutralize the toxin upon oral exposure. Mice immunized i.n. with the vaccine alone did not produce IgA.

TABLE 18

Induction of IgG1, IgG2a and IgA antibodies in BALB/c mice vaccinated intranasally (twice, 1 week apart) with free or CCS-associated *Clostridium botulinum* toxoid (CBT)

| | Mean antibody titer | | | | | |
|---|---|---|---|---|---|---|
| Vaccine[a] | Serum | | Small intestine | | | Feces |
| n = 10 | IgG1 | IgG2a | IgG1 | IgG2a | IgA | IgA |
| CBT | 0 | 0 | 1000 | 180 | 0 | 0 |
| CCS-CBT | 400 | 24 | 1600 | 0 | 1800 | 1800 |

Materials

Chemistry

Synthesis of N-palmitol D-erthro sphingosyl-1-carbamoyl Spermine (CCS)

(i) N-palmitoylsphingosine (1.61 g, 3 mmol) was dissolved in dry THF (100 ml) with heating. The clear solution was brought to room temperature and N,N'-disuccinimidyl carbonate (1.92 g, 7.5 mmol) was added. DMAP (0.81 g, 7.5 mmol) was added with stirring and the reaction further stirred for 16 hours. The solvent was removed under reduced pressure and the residue re-crystallized from n-heptane yielding 1.3 g (68%) of disuccinimidylceramidyl carbonate as white powder m.p. 73-76° C.

(ii) Spermine (0.5 g, 2.5 mmol) and the disuccinimidylceramidyl carbonate (0.39 g, 0.5 mmol) were dissolved in dry dichloromethane with stirring and then treated with catalytic amount of 4-dimethylamino pyridine (DMAP). The solution was stirred at room temperature for 16 hours, the solvent evaporated and the residue treated with water, filtered and dried in vacuo, giving 0.4 g (82%) of crude material which was further purified by column chromatography on Silica gel, using 60:20:20 Butanol:AcOH:$H_2O$ eluent.

(iii) For obtaining a quaternary amine within the compound, the product of step (ii) may be methylated with DMS or $CH_3I$.

The structure of CCS was confirmed by $^1H$- and $^{13}C$-NMR spectrometry (data not shown).

Other Synthetic Procedures

Similarly to the above procedure, the following procedures may be applied:

Synthesis of Linear Monosubstituted Ceramde-Spermine Conjugate as Depicted in FIG. 1A An equivalent of a ceramide is reacted with 2.5 equivalents of disuccinimidyl carbonate in the presence of DMAP to obtain the corresponding 1,3-di-O-succinimidyl derivative is obtained.

The disuccinimidyl derivative though obtained is reacted with an equivalent of spermine at room temperature using catalytic amount of DMAP to obtain the 3-monosubstituted ceramide-spermine conjugate of FIG. 1B.

Synthesis of Linear Disusbstituted Ceramide-Spermine Conjugate as Depicted in FIG. 1B An equivalent of 1,3-di-O-succinimidyl sphinogid derivative prepared as described above is reacted with 2.5 equivalents of spermine at 800 in the presence of catalytic amounts of DMAP. The 1,3-disubstituted CCS is though obtained.

Synthesis of Linear Disusbstituted Ceramide-Branched Spermine Conjugate as Depicted in FIG. 1C An equivalent of 1,3-di-O-succinimidyl ceramide derivative prepared as described above is reacted with 2.5 equivalents of alpha-omega di protected spermine at 80° in the presence of catalytic amounts of DMAP.

The protection is removed and the 1,3-"branched" disubstituted ceramide-spermine conjugate is obtained.

Synthesis of Linear Disusbstituted Ceramide—Cyclic Spermine Conjugate as Depicted in FIG. 1D An equivalent of 1,3-di-O-succinimidyl ceramide derivative prepared as described above is reacted with 0.75 equivalents of spermine at 80° C. in the presence of catalytic amounts of DMAP.

Influenza Antigens

A monovalent subunit antigen preparation derived from influenza A/New Caledonia/20/99-like (H1N1) strain was generously provided by Drs. Gluck and Zurbriggen, Berna Biotech, Bern, Switzerland. This preparation (designated herein H) comprised of 80-90% hemagglutinin, 5-10 wt % neuraminidase and trace amounts of NP and Ml proteins. A commercial trivalent subunit vaccine (Fluvirin®) for the 2003/2004 season containing HN derived from A/New Caledonia/20/99 (H1N1), A/Panama/2007/99 (H3N2) and B/Shangdong/7/97 was obtained from Evans Vaccines Ltd., Liverpool, UK. This vaccine was concentrated ~x8 (Eppendorf Concentrator 5301, Eppendorf AG, Hamburg, Germany) prior to encapsulation. A whole inactivated virus was used in some experiments for in vitro stimulation.

Lipids

The phospholipids (PL) dimyristoyl phosphatidylcholine (DMPC), dimyristoyl phosphatidylglycerol (DMPG), and dioleoyl phosphatidylethanolamine (DOPE) are from Lipoid GmbH, Ludwigshafen, Germany. In addition to DMPC (neutral) and DMPC/DMPG (9/1 mole ratio, anionic) liposomes, 6 formulations of cationic liposomes/lipid assemblies were prepared. The monocationic lipids dimethylaminoethane carbamoyl cholesterol (DC-Chol), 1,2-distearoyl-3-trimethylammonium-propane (chloride salt) (DSTAP), dioleoyl-3-trimethylammonium-propane (chloride salt) (DOTAP), and dimyristoyl-3-trimethylammonium-propane (chloride salt) (DMTAP) are from Avanti Polar Lipids (Alabaster, Ala., USA). The monocationic lipid dimethyldioctadecylammonium bromide (DDAB) and cholesterol (Chol) are from Sigma. The novel, proprietary polycationic sphingolipid N-palmitoyl D-erythro sphingosyl carbamoyl-spermine (acetate salt) (ceramide carbamoyl-spermine, CCS) is from Biolab Ltd., Jerusalem, Israel. Where indicated, the helper lipids (DOPE, Chol) were used at a lipid/helper ratio of 1/1 to 4/1 mole ratio.

Mice

Specific pathogen-free (SPF) female BALB/c mice, 6-8 weeks old, and C57BL/6 mice, 18 month-old, were used (5-10 per group). Animals were maintained under SPF conditions.

Methods

Encapsulation of Influenza Antigens in Liposomes/Lipid Assemblies

HN antigens (see above) were encapsulated in large (mean diameter 0.1-5 μm) heterogeneous (unsized) vesicles. The following procedure was used routinely for the preparation of all vaccine formulations. Lipids (10-30 mg) were dissolved in 1 ml tertiary butanol, then sterilized by filtration (GF92, Glasforser, Vorfilter no. 421051, Schleicher & Schuell, Dassel, Germany). The sterile lipid solution was frozen at −70° C., then lyophilized for 24 h to complete dryness. The dried lipids could be stored at 4° C. for >2 years without significant (<5%) lipid degradation or loss of "encapsulation" capability. Upon need, the lipid powder was hydrated with the antigen solution (in PBS pH 7.2) at a lipid:antigen (protein) w/w ratio of 3/1 to 800/1. The antigen solution was added stepwise in increments of 20-50 III and vortexed vigorously after each addition, up to a final volume of 0.5-1 ml. In some experiments, the dried lipids were hydrated with PBS and the preformed "empty" lipid assemblies were mixed with the antigen solution. The mixture was vortexed for 1-2 min and used as is within 30-60 min.

To determine "encapsulation" efficiency, two procedures were used, depending on the formulation, resulting in ≥80% separation between the free antigen and the lipid-associated antigen. For all vaccine formulations, except CCS, the following separation technique was used. The lipid assemblies (1-30 mg lipid) containing the HN antigen (50-100 μg protein) were suspended in 0.5 ml PBS and carefully loaded over 0.5 ml of $D_2O$ (99.9%, Aldrich Chemical Co., Milwaukee, Wis., USA). The sample was then centrifuged for 1 h at 30° C. at 45,000 rpm. The free, non-encapsulated HN precipitates while the assembled (liposomal), HN and protein-free assemblies/liposomes remain in the supernatant. The entire supernatant was collected and the assemblies/liposomes were dissolved by adding 0.2 ml of warm 10% Triton X-100 to both the supernatant and the pellet fractions. Protein concentration in both fractions was determined by the modified Lowry technique. For the CCS formulation, the CCS-HN was suspended in 0.5 ml of PBS-$D_2O$ (1 vol PBS×10+9 vol $D_2O$) then mixed with 0.5 ml of PBS. The mixture was then centrifuged for 10 min at 20° C. at 10,000 rpm. The CCS+/−antigen precipitates while the free HN remains in the supernatant. Lipid dissolution and protein determination in both fractions were carried out as described above. In both separation techniques, the overall recovery of the HN antigens was >95%.

Immunization

Free (F-HN) and assembled/liposomal (Lip-HN) vaccines, 0.25-4 μg antigen/strain/dose and 0.075-1.2 mg lipid/dose, were administered either once intramuscularly (i.m., in 30 μl), once or twice intranasally (i.n., in 5-50 μl per nostril) spaced 3, 7 or 14 days apart, or twice orally (in 50 μl) spaced 1 week apart. In all cases, mice were lightly anesthetized with 0.15 ml of 4% chloral hydrate in PBS given intraperitoneally. For oral vaccination mice were treated orally with 0.5 ml of an antacid solution (8 parts Hanks' balanced salt solution+2 parts 7.5% sodium bicarbonate) 30 min prior to vaccination. Cholera toxin (CT, Sigma, USA), 1 μg/dose, was used in all experiments as a standard mucosal adjuvant for comparison. In two experiments, CpG-ODN (ODN 1018, generously provided by Dr. E. Raz, University of California, San Diego, Calif., USA), free and liposomal, 10 μg/dose, was used as an adjuvant.

Assessment of Humoral Responses

Sera, lung homogenates and nasal washes were tested, individually or pooled, 4-6 weeks post-vaccination, starting at 1/10 or 1/20 sample dilution. Hemagglutination inhibiting antibodies were determined by the standard hemagglutination inhibition (HI) assay, starting at 1/10 sample dilution. Mice with HI titer ≥40 (considered a protective titer in humans) were defined as seroconverted. Antigen-specific IgG1, IgG2a, IgA and IgE levels were measured by ELISA. The highest sample dilution yielding absorbance of 0.2 OD above the control (antigen+normal mouse serum, OD<0.1) was considered the ELISA antibody titer.

Assessment of Cellular Responses

Splenocytes obtained at 5-6 weeks after vaccination were tested for proliferative response, IFNγ and IL-4 production, and cytotoxic activity, following in vitro stimulation with the antigen. Cultures were carried out at 37° C. in enriched RPMI 1640 or DMEM medium supplemented with 5% (for proliferation, cytokines) or 10% (for cytotoxicity) fetal calf serum (FCS), with (for cytotoxicity) or without $5\times10^{-5}$ M 2-mercaptoethanol. Cell cultures were performed as follows: (i) Proliferation: $0.5\times10^6$ cells per well were incubated in U-shaped 96-well plates, in triplicate, with or without the antigen (0.5-5 μg per well), in a final volume of 0.2 ml. After 72-96 h, cultures were pulsed with 1 μCi $^3$H-thymidine for 16 h. Results are expressed in Δcpm=(mean counts per minute of cells cultured with antigen)−(mean counts per minute of cells cultured without antigen). (ii) Cytokines: $2.5\times10^6$ to $5\times10^6$ cells per well were incubated in 24-well plates, in duplicate, with or without the antigen (5-10 μg per well), in a final volume of 1 ml. Supernatants were collected after 48-72 h and tested by ELISA for murine IFNγ and IL-4 using the Opt EIA Set (Pharmingen, USA). (iii) Cytotoxicity: Responding splenocytes ($2.5\times10^6$) were incubated as in (ii) for 7 days together with an equal number of stimulating BALB/c splenocytes that had been infected with the X/127(H1N1) influenza virus (see below). For infection, the splenocytes were incubated, with occasional stirring, for 3 h at 37° C. in RPMI 1640 medium (without FCS) with 150 hemagglutination units/$1\times10^6$ splenocytes of the virus, followed by washing. Subsequently, the primed effector cells were restimulated for 5 days with infected, irradiated (3,000 rad) splenocytes at an effector/stimulator cell ratio of 1/4 in the presence of 10 IU/ml of rhIL-2. Cytotoxicity was measured using the standard 4 h $^{51}$Cr release assay at an effector/target cell ratio of 100/1. The labeled target cells used were unmodified P815 and P815 pulsed for 90 min at 37° C. with the HA2 189-199 peptide (IYSTVASSLVL, 20 μg/$1\times10^6$ cells).

Determination of Protective Immunity

Mice were anesthetized and 25 μl of live virus suspension per nostril, ~$10^7$ EID 50' (egg-infectious dose 50%), was administered, using the reassortant virus X-127 (A/Beijing/262/95 (H1N1)×X-31 (A/Hong Kong/1/68×A/PR/8/34), which is infectious to mice and cross-reactive with A/New Caledonia. The lungs were removed on day 4, washed thrice in cold PBS, and homogenized in PBS (1.5 ml per lungs per mouse, referred to as 1/10 dilution). Homogenates of each group were pooled and centrifuged at 2000 rpm for 30 min at 4° C. and the supernatants collected. Serial 10-fold dilutions were performed and 0.2 ml of each dilution was injected, in duplicate, into the allantoic sac of 11-day-old embryonated chicken eggs. After 48 h at 37° C. and 16 h at 4° C., 0.1 ml of allantoic fluid was removed and checked for viral presence by hemagglutination (30 min at room temperature) with chicken erythrocytes (0.5 wt. %, 0.1 ml). The lung virus titer is determined as the highest dilution of lung homogenate producing virus in the allantoic fluid (positive hemagglutination).

Biodistribution and Pharmacokinetics of Various Fluorescently-Labeled-Lipid Formulations and Radioactively-Labeled HN Antigen Mice were vaccinated once with lissamine-rhodamine labeled lipid assembly formulations either empty or associated with trivalent subunit influenza vaccine (HN) in a volume of 20 μl. After 1, 5 or 24 hours, mice were sacrificed and various organs were removed. The organs were stored at −20 deg overnight, and the next morning homogenized in lysis buffer. 0.2 ml the subsequent homogenate was transferred to eppendorf tubes, 0.8 mL of isopropanol was added, and spun for 15 minutes to release fluorescent probe into the supernatant. 50 uL of the supernatant was loaded onto a 384 black plate and the fluorescence was read (Em: 545, Ex: 596).

In a further assay, 450 μg of trivalent HN vaccine (in 5 mL) were dialysed against DDW (to remove salt) and then concentrated ×1000 to 5 μL. The protein was then diluted in 0.1M borate buffer (pH 8.5) to a stock solution of 450 μg in 15 μL. The protein was then labeled with $^{125}I$ using the Bolton Hunter reagent, according to the manufacturer's instructions. Mice were provided with the 125I-labeled HN (2 μg) and at 1, 5 and 24 hrs, the mice were sacrificed, and various organs (see FIG. 3) were removed into vials and read in a γ-counter calibrated for $^{125}I$.

The invention will now be defined by the appended claims, the contents of which are to be read as included within the disclosure of the specification.

The invention claimed is:

1. A composition comprising an amount of sphingoid-polyalkylamine conjugate and an amount of an immune response stimulating or enhancing biologically active molecule, wherein said biologically active molecule is an antigenic protein, an antigenic peptide, an antigenic polypeptide, or an oligodeoxynucleotide, and wherein said sphingoid-polyalkylamine conjugate comprises a sphingoid backbone carrying, via a carbamoyl bond, at least one polyalkylamine chain, said sphingoid-polyalkylamine conjugate having the following formula (I):

(I)

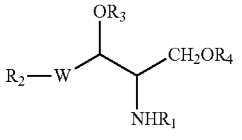

wherein $R_1$ represents a hydrogen, a branched or linear alkyl, aryl, alkylamine, or a group —C(O)$R_5$;

$R_2$ and $R_5$ represent, independently, a branched or linear $C_{10}$-$C_{24}$ alkyl, alkenyl or polyenyl group;

$R_3$ is hydrogen or a group —C(O)—N$R_6R_7$, and $R_4$ is, independently, a group —C(O)—N$R_6R_7$, in which $R_6$ and $R_7$, being the same or different for $R_3$ and $R_4$, represent, independently, a hydrogen, or a saturated or unsaturated branched or linear polyalkylamine, wherein one or more amine units in said polyalkylamine may be a quaternary ammonium, and wherein at least one of $R_3$ and/or $R_4$ comprises said polyalkylamine; or $R_3$ and $R_4$ form, together with the oxygen atoms to which they are bound, a heterocyclic ring comprising —C(O)—N$R_9$—[$R_8$—N$R_9$]$_m$—C(O)—, in which $R_8$ represents a saturated or unsaturated $C_1$-$C_4$ alkyl and $R_9$ represents a hydrogen or a polyalkylamine of the formula —[$R_8$—N$R_9$]$_n$—, wherein said $R_9$ or each alkylamine unit —$R_8$N$R_9$ may be the same or different in said polyalkylamine; and n and m represent, independently, an integer from 1 to 10; and W represents a —CH═CH—, —$CH_2$—CH(OH)— or —$CH_2$—$CH_2$— group.

2. The composition of claim 1, further comprising an immunostimulating agent.

3. The composition of claim 1, wherein the sphingoid of said sphingoid backbone is selected from the group consisting of ceramide, dihydroceramide, phytoceramide, dehydrophytoceramide, ceramine, dihydroceramine, phytoceramine, and dehydrophytoceramine.

4. The composition of claim 3, wherein the sphingoid of said sphingoid backbone is ceramide.

5. The composition of claim 1, wherein said polyalkylamine chain is spermine, spermidine or a polyalkylamine analog of spermine or spermidine.

6. The composition of claim 1, wherein said sphingoid-polyalkylamine conjugate is N-palmitoyl D-erythro sphingosyl carbamoyl-spermine (CCS).

7. The composition of claim 6, wherein said biologically active molecule is a molecule derived from influenza virus or is an analog of a molecule derived from influenza virus, which analog comprises any substance which includes an influenza derived antigenic fragment that elicits an immune response.

8. The composition of claim 1, wherein $R_1$ represents a —C(O)$R_5$ group, $R_5$ being as defined.

9. The composition of claim 1, wherein said $R_2$ and $R_5$ represent, independently, a linear or branched $C_{12}$-$C_{18}$ alkyl or alkenyl group.

10. The composition of claim 1, wherein W represents —CH═CH—.

11. The composition of claim 1, wherein $R_1$ represents a —C(O)$R_5$ group; $R_5$ represents a $C_{12}$-$C_{18}$ linear or branched alkyl or alkenyl; W represents —CH═CH—; $R_2$ represents a $C_{12}$-$C_{18}$ linear or branched alkyl or alkenyl; $R_3$ and $R_4$ represent, independently, a group —C(O)—N$R_6R_2$, and $R_3$ may also represent a hydrogen, wherein $R_6$ and $R_7$ represent, independently, a hydrogen or a polyalkylamine having the general formula (II):

$$-[R_8-NR_9]_n-H$$

wherein $R_8$ represent a $C_1$-$C_4$ alkyl;

$R_9$ represents a hydrogen or a polyalkylamine branch of formula (II), said $R_8$ and $R_9$ may be the same or different for each alkylamine unit, —$R_8$N$R_9$—, in the polyalkylamine of formula (II); and n represents an integer from 3 to 6.

12. The composition of claim 1, wherein $R_3$ is a hydrogen atom.

13. The composition of claim 1, wherein both $R_3$ and $R_4$ represent the same or a different polyalkylamine.

14. The composition of claim 1, wherein $R_1$ represents a —C(O)$R_5$ group; $R_5$ represents a $C_{12}$-$C_{18}$ linear or branched alkyl or alkenyl; W represents —CH═CH—; $R_2$ represents a $C_{12}$-$C_{18}$ linear or branched alkyl or alkenyl; $R_3$ and $R_4$ represent, independently, a group —C(O)—$NR_6R_7$, wherein $R_6$ and $R_7$ represent, independently, an alkylamine or a polyalkylamine having the general formula (II):

$$-\!\!\left[R_8-NR_9\right]_n H$$

wherein $R_8$ represents a $C_1$-$C_4$ alkyl;

$R_9$ represents a hydrogen or a polyalkylamine branch of formula (II), said $R_8$ and $R_9$ may be the same or different for each alkylamine unit, —$R_8NR_9$—, in the polyalkylamine of formula (II); and n represents an integer from 3 to 6.

15. The composition of claim 1, wherein $R_1$ represents a —C(O)$R_5$ group; $R_5$ represents a $C_{12}$-$C_{18}$ linear or branched alkyl or alkenyl; W represents —CH═CH—; $R_2$ represents a $C_{12}$-$C_{18}$ linear or branched alkyl or alkenyl; $R_3$ and $R_4$ form together with the oxygen atoms to which they are bonded a heterocyclic ring comprising —C(O)—[NH—$R_8$]$_n$—NH—C(O)—, wherein $R_8$ represents a $C_1$-$C_4$ alkyl, and wherein for each alkylamine unit having the formula —NH—$R_8$—, said $R_8$ may be the same or different; and n represents an integer from 3 to 6.

16. The composition of claim 1, wherein said $R_8$ is a $C_3$-$C_4$ alkyl.

17. A composition according to claim 1, wherein said biologically active molecule is an oligodeoxynucleotide (ODN).

18. A method for stimulating or enhancing the immune response of a subject, the method comprising administering to said subject an effective amount of a composition according to claim 1.

19. The method of claim 18, wherein, in said composition, said biologically active molecule is associated with said sphingoid-polyalkylamine conjugate.

20. The method of claim 18, wherein, in said composition, said biologically active molecule has, at a physiological pH, a net negative dipole moment, a net negative charge or contains at least one region having a net negative charge.

21. The method claim 18, wherein, in said composition, said biologically active molecule is an antigenic protein, an antigenic peptide, or an antigenic polypeptide.

22. The method claim 18, wherein, in said composition, said biologically active molecule is an oligodeoxynucleotide (ODN).

23. The method of claim 18, further comprising administering to said subject an immunostimulating agent.

24. The method of claim 23, wherein said immunostimulating agent is administered concomitant with, or within a time interval before or after administration of said sphingoid-polyalkylamine conjugate.

25. The method of claim 18, wherein, in said composition, said sphingoid-polyalkylamine conjugate forms a lipid assembly.

26. The method of claim 25, wherein said lipid assembly comprises vesicles or micelles or a combination of same.

27. The method of claim 26, wherein said biologically active molecule is associated with said lipid assembly.

28. The method of claim 18, wherein, in said composition, the sphingoid of said sphingoid backbone is selected from the group consisting of ceramide, dihydroceramide, phytoceramide, dehydrophytoceramide, ceramine, dihydroceramine, phytoceramine, and dehydrophytoceramine.

29. The method of claim 28, wherein the sphingoid of said sphingoid backbone is ceramide.

30. The method of claim 29, wherein said polyalkylamine chain is spermine, spermidine, a polyamine analog or a combination thereof.

31. The method of claim 18, wherein, in said composition, said sphingoid-polyalkylamine conjugate is N-palmitoyl D-erythro sphingosyl carbamoyl-spermine (CCS).

32. The method of claim 18, wherein, in said composition, $R_1$ represents a —C(O)$R_5$ group.

33. The method of claim 18, wherein, in said composition, said $R_2$ and $R_5$ represent, independently, a linear or branched $C_{12}$-$C_{18}$ alkyl or alkenyl group.

34. The method of claim 18, wherein, in said composition, W represents —CH═CH—.

35. The method of claim 18, wherein, in said composition, $R_1$ represents a —C(O)$R_5$ group; $R_5$ represents a $C_{12}$-$C_{18}$ linear or branched alkyl or alkenyl; W represents —CH═CH—; $R_2$ represents a $C_{12}$-$C_{18}$ linear or branched alkyl or alkenyl; $R_3$ and $R_4$ represent, independently, a group —C(O)—$NR_6R_7$, and $R_3$ may also represent a hydrogen, wherein $R_6$ and $R_7$ represent, independently, a hydrogen or a polyalkylamine having the general formula (II):

$$-\!\!\left[R_8-NR_9\right]_n H$$

wherein $R_8$ represent a $C_1$-$C_4$ alkyl;

$R_9$ represents a hydrogen or a polyalkylamine branch of formula (II), said $R_8$ and $R_9$ may be the same or different for each alkylamine unit, —$R_8NR_9$—, in the polyalkylamine of formula (II); and n represents an integer from 3 to 6.

36. The method of claim 35, wherein $R_3$ is a hydrogen atom.

37. The method of claim 18, wherein, in said composition, both $R_3$ and $R_4$ represent the same or a different polyalkylamine.

38. The method of claim 18, wherein, in said composition, $R_1$ represents a —C(O)$R_5$ group; $R_5$ represents a $C_{12}$-$C_{18}$ linear or branched alkyl or alkenyl; W represents —CH═CH—; $R_2$ represents a $C_{12}$-$C_{18}$ linear or branched alkyl or alkenyl; $R_3$ and $R_4$ represent, independently, a group —C(O)—$NR_6R_7$, wherein $R_6$ and $R_7$ represent, independently, an alkylamine or a polyalkylamine having the general formula (II):

$$-\!\!\left[R_8-NR_9\right]_n H$$

wherein $R_8$ represents a $C_1$-$C_4$ alkyl;

$R_9$ represents a hydrogen or a polyalkylamine branch of formula (II), said $R_8$ and $R_9$ may be the same or different for each alkylamine unit, —$R_8NR_9$—, in the polyalkylamine of formula (II); and n represents an integer from 3 to 6.

39. The method of claim 18, wherein, in said composition, $R_1$ represents a —C(O)$R_5$ group; $R_5$ represents a $C_{12}$-$C_{18}$ linear or branched alkyl or alkenyl; W represents —CH═CH—; $R_2$ represents a $C_{12}$-$C_{18}$ linear or branched alkyl or alkenyl; $R_3$ and $R_4$ form together with the oxygen atoms to which they are bonded a heterocyclic ring comprising —C(O)—[NH—$R_8$]$_n$—NH—C(O)—, wherein $R_8$ represents a $C_1$-$C_4$ alkyl, and wherein for each alkylamine unit having the formula —NH—$R_8$—, said $R_8$ may be the same or different; and n represents an integer from 3 to 6.

40. The method of claim 39, wherein, in said composition, said $R_8$ is a $C_3$-$C_4$ alkyl.

41. The method of claim 18, wherein, in said composition, said biologically active molecule is derived from influenza virus or an analog of a molecule derived from influenza virus.

42. The method of claim 41, wherein said biologically active molecule is a combination of hemagglutinin and neuraminidase (HN).

43. The method of claim 18, comprising intranasal or intramuscular administration of said composition.

44. The method of claim 31, comprising intranasal or intramuscular administration of said N-palmitoyl D-erythro sphingosyl carbamoyl-spermine together with said biologically active molecule.

45. A method for stimulating or enhancing the immune response of a subject to influenza virus, the method comprising administering to the subject an effective amount of N-palmitoyl D-erythro sphingosyl carbamoyl-spermine (CCS) together with an influenza antigen.

46. A composition comprising an amount of sphingoid-polyalkylamine conjugate and an amount of an immune response stimulating or enhancing biologically active molecule, wherein the biologically active molecule is a nucleic acid molecule or a protein, polypeptide or peptide, and wherein said sphingoid-polyalkylamine conjugate has the following formula (I):

(I)

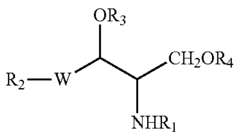

wherein $R_1$ represents a hydrogen, a branched or linear alkyl, aryl, alkylamine, or a group —C(O)$R_5$;

$R_2$ and $R_5$ represent, independently, a branched or linear $C_{10}$-$C_{24}$ alkyl, alkenyl or polyenyl group;

$R_3$ is hydrogen or a group —C(O)—$NR_6R_7$, and $R_4$ is, independently, a group —C(O)—$NR_6R_7$, in which $R_6$ and $R_7$, being the same or different for $R_3$ and $R_4$, represent, independently, a hydrogen, or a saturated or unsaturated branched or linear polyalkylamine, wherein one or more amine units in said polyalkylamine may be a quaternary ammonium, and wherein at least one of $R_3$ and/or $R_4$ comprises said polyalkylamine; or $R_3$ and $R_4$ form, together with the oxygen atoms to which they are bound, a heterocyclic ring comprising —C(O)—$NR_9$—[$R_8$—$NR_9$]$_m$—C(O)—, in which $R_8$ represents a saturated or unsaturated $C_1$-$C_4$ alkyl and $R_9$ represents a hydrogen or a polyalkylamine of the formula —[$R_8$—$NR_9$]$_n$—, wherein said $R_9$ or each alkylamine unit —$R_8NR_9$ may be the same or different in said polyalkylamine; and n and m represent, independently, an integer from 1 to 10; and W represents a —CH═CH—, —$CH_2$—CH(OH)— or —$CH_2$—$CH_2$— group.

47. The composition of claim 46, further comprising an immunostimulating agent.

48. A method for stimulating or enhancing the immune response of a subject, the method comprising administering to said subject an effective amount of a composition according to claim 46.

49. The method of claim 48, wherein, in said composition, said biologically active molecule is a nucleic acid molecule.

* * * * *

UNITED STATES PATENT AND TRADEMARK OFFICE

CERTIFICATE OF CORRECTION

PATENT NO. : 8,673,285 B2
APPLICATION NO. : 10/560928
DATED : March 18, 2014
INVENTOR(S) : Yechezkel Barenholz et al.

It is certified that error appears in the above-identified patent and that said Letters Patent is hereby corrected as shown below:

In the Claims

In claim 11, column 34, line 46, delete "$-C(O)-NR_6R_2$" and insert -- $-C(O)-NR_6R_7$ --.

Signed and Sealed this
Eighth Day of July, 2014

Michelle K. Lee

Michelle K. Lee
*Deputy Director of the United States Patent and Trademark Office*